United States Patent

Ushio et al.

[11] Patent Number: 6,108,096
[45] Date of Patent: Aug. 22, 2000

[54] LIGHT ABSORPTION MEASUREMENT APPARATUS AND METHODS

[75] Inventors: Yoshijiro Ushio, Yokohama; Toru Nakamura, Kawasaki; Sumito Shimizu, Yokohama; Tetsuya Oshino, Kawasaki, all of Japan

[73] Assignee: Nikon Corporation, Tokyo, Japan

[21] Appl. No.: 09/217,332

[22] Filed: Dec. 21, 1998

[51] Int. Cl.[7] .................................................. G01N 21/00
[52] U.S. Cl. ........................................ 356/432; 356/440
[58] Field of Search ............................ 356/432, 440, 356/244; 250/215

[56] References Cited

U.S. PATENT DOCUMENTS 5,151,590  9/1992  Takamoto et al. ...................... 356/432
5,596,146  1/1997  Waller et al. ........................... 356/432
5,673,114  9/1997  Ushio ..................................... 356/432

*Primary Examiner*—Frank G. Font
*Attorney, Agent, or Firm*—Klarquist Sparkman Campbell Leigh & Whinston, LLP

[57] ABSTRACT

Apparatus and methods are disclosed for measuring changes in light absorption of a sample optical component. The sample is held in a sample holder in a sample chamber during irradiation by an intense light, usually pulsatile light. Molecules of a gas are introduced into the sample chamber as the sample is irradiated. The molecules can be of a material suspected to become adhered to or absorbed by the sample in a way that causes an undesired change in light absorption by the sample. Changes in light absorption by the sample are preferably measured photoacoustically. The molecules of the gas can be generated by controlled irradiation of a "source material" with a light (which can be the same as used to irradiate the sample) sufficient to generate such molecules of gas from the source material, and routing the gaseous molecules to the sample as the sample is irradiated.

38 Claims, 10 Drawing Sheets

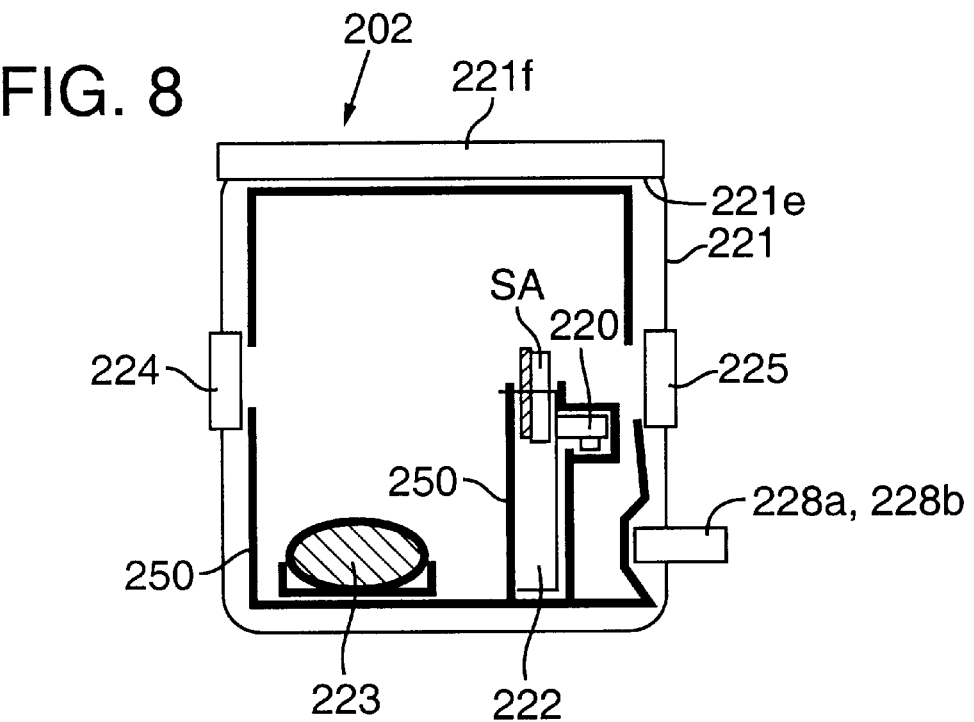

LIGHT ABSORPTION MEASUREMENT APPARATUS AND METHODS

FIELD OF THE INVENTION

This invention pertains to apparatus and methods for measuring changes in light absorption by an optical component due to exposure of the optical member to light, especially high-intensity short-wavelength light. The invention also pertains to apparatus and methods for measuring such changes on the surface of an optical component versus such changes in the interior of the optical member due to adhesion to the surface or absorption by the surface of molecules of a substance (such as a gas) causing a surficial change in light absorption of the optical component.

BACKGROUND OF THE INVENTION

The performance demands being placed on optical components are increasing rapidly with rapid changes in optical technology. This situation is driving rapid changes in methods for testing the ability of optical components to withstand the rigors of modern optical applications. Such optical components include, but are not limited to, any of various optical elements used in optical systems or used singly for optical purposes, optical elements having an antireflective or other coating, and transmissive and reflective optical elements including photomasks and substrates for use in microlithography.

Particular concern is directed to the long-term stability of optical performance of optical components exposed to extremely long or extremely short wavelengths of light compared to visible light. For example, very short wavelengths (<200 nm) of light generated by any of the various types of excimer lasers are being increasingly employed in optical systems in which the short, high-intensity light is useful for producing improved image resolution. Such systems include laser-processing devices, and microlithography apparatus such as steppers.

In any event, such extreme wavelengths of light (compared to visible light) place severe demands on optical components. This poses a widespread need for methods and systems for measuring and evaluating damage to, or other undesirable change in performance of, optical components from exposure to such wavelengths.

Photons of short-wavelength light have higher energy than photons of visible light and are generally more likely to interact with an object on which such light impinges. Such interaction can result in a progressive degradation of an optical property of the object, such as an increase in light absorption and an accompanying decrease in light transmission through the object. Degradation in an optical property can have enormous impact on the suitability of the optical component for a particular use. Therefore, it is very important to be able to measure and evaluate such degradation as part of the engineering effort required to design an optical system.

Many optical components are surficially coated to reduce reflections, for example. Hence, a degradation of optical performance of an optical component may be caused by damage or other undesirable change to the coating rather than, or in addition to, damage to the component itself. In addition, optical components used in a particular atmosphere or other environmental condition may exhibit a performance degradation due to light-induced changes to residual lens-polishing material or other substance adhering to or absorbed by the optical component.

Performance degradation due to a change in a physical property of an optical component is typically progressive and can be due to factors such as radiation-induced heating (i.e., heating caused by irradiation) and damaging effects of the electric-field component of high-intensity short-wavelength light irradiated onto the optical component. Hence, it is important to be able to evaluate changes in optical performance of an optical component over time or otherwise with cumulative exposure to light. Conventional methods for performing such evaluations include destructive test methods such as laser-damage threshold (LDT) testing.

As noted above, degradation in an optical property (such as a reduction in transmittance or reflectivity) can arise from surficial adhesion and/or absorption of a contaminating material from the environment, a phenomenon termed "fogging" or "clouding". Fogging can arise not only in optical elements comprising an optical system (e.g., projection-optical system) but also in any of various materials used in conjunction with the optical elements (e.g., lens mountings, antireflective coatings, or photoresist films used in microlithography).

Fogging can arise simply from placing an optical component in environmental contact with a culprit contaminant (capable of adhering to or absorbing into the optical component). In other cases, whether or not the contaminant adheres to or is absorbed by the optical component depends upon whether the optical component and/or contaminant is irradiated by light. The latter is generally understood to result from heating of the optical component or contaminant by exposure to the light, resulting in a photochemical reaction leading to fogging (e.g., by photochemically induced generation of a gas from the contaminant, wherein gas condenses or precipitates on the optical component). This problem is particularly acute in optical apparatus that use short-wavelength light which seems to aggravate the fogging phenomenon. Furthermore, optical components in such apparatus can be exposed to scattered light (as opposed to direct light) which can also lead to fogging.

Satisfactory methods and apparatus do not exist for evaluating fogging from adhesion and/or absorption of substances (e.g., organic substances) to optical components and the effect of such fogging on light absorption by the optical components, especially such phenomena not accompanied by visual damage to the components. Even slight fogging or other degradation that is not visually detectable can have a substantial effect on the performance of an optical component. By the time physically observable degradation is manifest, optical performance may have become profoundly reduced.

Conventional methods for evaluating the effects of light intensity on a sample employ light-intensity sensors. However, such methods have practical limits. For example, it is difficult to control and measure the stability and light output of a short-wavelength (e.g., 200 nm or less) light source. The resulting variability in obtained measurements makes it especially difficult to reliably measure small changes in light absorption by a sample optical component.

Other problems with conventional approaches include: (1) Whenever the subject light is being produced by a pulsed laser (e.g., excimer laser), the response of the light sensor is usually delayed relative to each received pulse. (2) It is difficult to separately measure a unit of light absorption by conventional optical methods because, inter alia, such measurements include the effect of light scattering from the surface irradiated by the light. (3) Conventional methods do not facilitate ascertaining the origin and effect of contaminant material adhering to and/or absorbed into the surface of the sample optical component as a result of thermal or photochemical reactions caused by light irradiation of a source of the contaminant material. (4) Although conventional methods include techniques of "optical cleaning" (by which optical components are removed from their mountings and any adhering matter is cleaned from the surfaces of the components using light), the optical components tend to become readily recontaminated after such cleaning.

Finally, although certain conventional testing methods involve exposing a sample optical component to unusually intense light so as to accelerate the effect of light exposure, there is a significant probability that the sample under such conditions will exhibit a change in light absorption due to color shifting and similar phenomena arising from the intensity of the light, and not due solely to cumulative exposure to the light. This problem is especially prevalent when the surface of the sample optical component is coated or is contaminated with adhering or absorbed matter. Under such conditions, if the light absorbed by the optical component itself exhibits a variation, such a variation is impossible to separate from a change in light absorption exhibited by the coating and/or a change in light absorption exhibited by a surficial contaminant. Furthermore, with respect to optical components coated with a thin film, accurate measurements of changes in absorption of the optical component are not obtainable because changes in light absorption also typically accompany degradation of the thin film with exposure to the same light.

A conventional attempt to solve this problem involves irradiating the component with light pulses and measuring, at various depths within the component, acoustic waves generated in the optical component due to exposure to the light pulses. The frequency of the light pulses is varied while changing the thermal diffusion conditions in an attempt to obtain light-absorption measurements at various depths within the sample optical component. However, when attempting to obtain measurements at extremely short wavelengths of light, it is conventionally not possible to irradiate using an intense light source while changing the frequency of the light. Consequently, this technique cannot be used reliably to quantitatively separate and evaluate changes in light absorption on the surface and changes in light absorption through the thickness dimension of the optical component.

SUMMARY OF THE INVENTION

According to a first aspect of the invention, apparatus are provided for measuring changes in light absorption exhibited by an optical component upon exposure of the optical component to light. According to one embodiment, such an apparatus comprises a sample holder, a sensor, a sample-chamber housing, and a gas-introduction port. The sample holder is configured to hold a sample optical component as the sample is exposed to light. The sensor is configured and situated to detect absorbance of light by the sample as the sample is exposed to the light. The sample-chamber housing defines a sample chamber configured to contain the sample holder holding the sample as the sample is exposed to the light. The gas-introduction port conducts a specified gas from a source into the sample chamber.

The apparatus can include a gas-inlet-control unit (such as, but not limited to, a gas-flow controller) situated and configured so as to regulate an amount of the specified gas introduced into the sample chamber through the gas-introduction port. The specified gas preferably comprises molecules that can attach to the sample in a way that can result in a change in light absorbance by the sample.

The housing can be configured to contain a source material of molecules that can attach to the sample in a way that can result in a change in light absorbance by the sample. Such a configuration can be in the form of a sub-chamber for holding the source material but not the sample. The sub-chamber can be separated from the sample chamber by a partition that blocks scattered light from passing from the sample chamber to the sub-chamber and from the sub-chamber to the sample chamber while allowing the molecules of the source material to pass from the sub-chamber to the sample chamber.

The housing can include a first window transmissive to a first light and a second window transmissive to a second light. The first window is preferably situated so as to allow the first light to pass through the first window to the sample in the sample chamber; the second window is preferably situated so as to allow the second light to pass through the second window to the source material in the sub-chamber. In any event, the housing preferably comprises a window transmissive to the light, wherein the window is situated so as to allow the light to pass from a light source external to the housing to the sample in the sample chamber.

If desired, a carrier gas can be used to help propel molecules of the source material to the sample, or can be used to dilute the molecules of the source material to a particular concentration.

The sensor preferably comprises a photoacoustic transducer and a fast-fourier-transform processor connected to the photoacoustic transducer.

Another embodiment of an apparatus according to the invention comprises a sample holder, a photoacoustic transducer, a sample chamber, and a gas-introduction port. The sample holder is configured to hold a sample optical component as the sample is exposed to pulses of light. The photoacoustic transducer is configured and arranged to detect photoacoustic signals generated by the sample as the sample is exposed to pulses of the light. The sample chamber is configured to contain the photoacoustic transducer and the sample holder holding the sample as the sample is exposed to the pulses of light. The gas-introduction port is used for conducting a specified gas from a source into a space defined by the sample chamber. The specified gas preferably comprises molecules that can adhere to or be absorbed by the sample.

The apparatus can include a source of the gas, wherein the source is connected to the gas-introduction port. The source of the gas can be a source chamber connected via a conduit to the gas-introduction port. The source chamber in such an embodiment is configured to contain a source material that, when irradiated by light, releases molecules of a compound that can adhere to or be absorbed by the sample in a way that can cause a change in light absorption by the sample.

The gas-introduction port can comprise a gas-inlet-control unit (such as, but not limited to, a gas-flow controller) situated and configured so as to regulate an amount of the gas introduced into the sample chamber through the gas-introduction port from the source.

The apparatus can include a gas sensor situated and configured to quantitatively determine a concentration of the specified gas in the space defined by the sample chamber.

The sample chamber can comprise a material exhibiting a predetermined degassing of molecules into the space. Alternatively or in addition, the sample chamber can comprise a lining, applied to the interior walls of the sample chamber, exhibiting a predetermined degassing of molecules into the space. Such a lining is made from a low-degassing material such as aluminum. The lining (or the sample chamber itself) is preferably cleanable or replaceable after each of one or more uses.

Yet another embodiment of an apparatus according to the invention comprises a first light source, a source chamber, a second light source, a sample holder, a sensor, and a sample chamber. The first light source is operable to produce a first light. The source chamber is configured to contain a source material as the source material is irradiated by the first light. The first light has a wavelength sufficient to cause the source material to produce, during such irradiation by the first light, molecules of an adhesion gas. The second light source is operable to produce pulses of a second light. The sample holder is preferably configured to hold a sample optical component as the sample is exposed to pulses of the second light. The sensor is configured and arranged to detect absorbance of the second light by the sample. The sample chamber defines a space, and is configured to contain within the space the sensor and the sample holder holding the sample as the sample is exposed to the pulses of the second light. A conduit is used for routing molecules of the adhesion gas from the source chamber to the sample chamber so as to expose the sample to the molecules of the adhesion gas as the sample is being exposed to the second light.

The apparatus can further comprise a light-intensity-adjustment optical system situated and configured to receive the second light and to adjust an intensity of the second light reaching the sample. The apparatus can further comprise a beamsplitter. Preferably, the source of the first light and the source of the second light are a pulsatile laser (e.g., an excimer laser). A first portion of a light beam produced by such a laser is reflected by the beamsplitter to become the first light and a second portion is transmitted by the beamsplitter to become the second light. A light blocker can be situated and configured to prevent stray light, including scattered light generated when the sample is irradiated by the second light, from irradiating the source material. The sensor preferably comprises a photoacoustic sensor in acoustic contact with the sample. The photoacoustic sensor is operable to measure an acoustic signal generated by expansion and contraction of the sample resulting from impingement on the sample of a pulse of the second light that causes an instantaneous heating a cooling of the sample.

The apparatus can include a gas analyzer or analogous component configured and situated to obtain data regarding identity and concentration of the adhesion gas.

Any of the apparatus summarized above enable one to analyze any of various culprit materials that can cause surficial contamination of a surface of an optical component in a way that causes the optical component to exhibit a change in light absorption. Sensitive measurements of any change in light absorption, especially over time as the optical component is irradiated with a train of light pulses, can be simply made using such apparatus. Furthermore, the sample can be exposed to gaseous molecules of a culprit material under controlled conditions as the sample is exposed to the light. Changes in light absorption caused by deposition of the material on the surface of the optical component can be monitored over time. In addition, comparative studies of optical components and surficial materials can be readily performed, which simplifies the task of specifying and qualifying particular materials for use as optical components and for use as surficial coatings for the optical coatings or other uses in the vicinity of the optical components.

Any of the apparatus according to the invention are also useful for examining the origin of material that adheres to or is absorbed by optical components whenever the optical components are irradiated using certain wavelengths of light. Such apparatus are also useful for determining specifically what wavelengths of light cause surficial contamination of optical components.

Any of the apparatus according to the invention also allow changes in light absorption within the thickness dimension of optical components, versus changes in light absorption of a surficial coating (e.g., antireflective coating) on the optical components, to be separately evaluated.

As used herein, an "optical component" can be an actual optical element as used in an optical system, or a sample of such an element specially configured for testing purposes.

Use of a change in temperature (non-radiant transition) of the sample is preferably used as a basis for measuring a change in light absorption of the sample mainly because a heat measurement can provide highly stable, rapid, and accurate determinations of a minute change in light absorption of a sample, especially with respect to short-wavelength light. Thus, similar to a calorimeter, a change in temperature of an optical component from absorption of light can be determined using a thermocouple, for example. Alternatively, a photoacoustic measurement approach can be employed. The photoacoustic approach detects deformations (normally volume expansions) occurring in the optical component itself or in the surrounding gaseous envelope of the optical component caused by a temperature change of the sample accompanying light absorption. Photoacoustic signals are also generated by the relaxation of the deformation occurring after the optical component has received a light pulse and the light pulse has ended. Amounts of light absorption can be calculated from such data.

Another approach for measuring changes in the absorption of light by a sample optical component is to measure a change in index of refraction of the sample caused by absorption of light. Such a change can be manifest as a change in the deflection of a light beam passing through the sample or a change in a parameter of the optical path assumed by a light beam passing through the sample.

In any event, the photoacoustic approach is preferred because of its relative simplicity of implementation and high measurement accuracy.

According to another aspect of the invention, methods are provided for measuring light absorption exhibited by an optical component sample as the optical component sample is irradiated with a light. In one representative embodiment of such a method, the sample is mounted in a sample holder. The sample and sample holder are placed in a sealed environment that can contain molecules of a gas that can adhere to or be absorbed by a surface of the sample. The sample is irradiated with pulses of a first light while exposing the sample to the molecules of the gas in the sealed environment containing molecules of the gas. As each pulse of the first light impinges on the sample, an acoustic signal generated in the sample due to exposure to the pulse is measured. The acoustic signal is a function of the amount of light energy absorbed by the sample from the light pulse. The method can further comprise the step of generating an electrical signal corresponding to the acoustic signal. A fast fourier transform of the electrical signal can be performed to separate out desired frequency components of the signal.

The method can also include the steps of irradiating a source material with a second light to cause the source material to produce molecules of the gas, and conducting the molecules of the gas to the sealed environment so as to contact the sample as the sample is being exposed to the first light in the sealed environment.

According to another embodiment of a method according to the invention, a sealable sample chamber is provided, and a sample is sealed in the sample chamber. Molecules of an "adhesion gas" (a gas comprising molecules that can adhere to or be absorbed by the optical component) are introduced into the sample chamber, preferably as the sample in the sample chamber is irradiated with pulses of a light suspected of causing the sample to exhibit a change in absorption of the first light with cumulative exposure of the sample to pulses of the light. Absorption of light by the sample is measured.

The sample chamber used in the foregoing embodiment is preferably defined by walls that exhibit low degassing. To such end, the walls of the sample chamber can be lined with a material exhibiting low degassing.

According to yet another method embodiment, a sample optical component is irradiated with a pulse of a light suspected of causing the sample to exhibit a change in absorption of the light with cumulative exposure of the sample to pulses of the light. As the pulse of the light impinges on the sample, an acoustic signal, generated in the sample due to exposure to the pulse, is measured. The acoustic signal has a waveform that is a function of an amount of light energy absorbed by the sample from the light pulse. The acoustic signal is generated by an expansion and contraction of the sample due to an instantaneous heating of the sample as the sample receives and absorbs at least a portion of the light pulse and a subsequent cooling of the sample after the light pulse. From the waveform, generated as the sample received the pulse of the light, first and second waveform components are determined. The first waveform component arises from absorption of light from the pulse on a surface of the sample. The second waveform component arises from absorption of light from the pulse within a depth dimension of the sample.

The first waveform component can be separated from the second waveform component, and the first and second waveform components can be broken down into respective constituent frequency components. The amplitude of the frequency components of the first waveform can be compared with the amplitude of the frequency components of the second waveform. Such information can be compared with information obtained previously with the same sample but from an earlier pulse irradiated on the sample. Alternatively, such information can be compared with information obtained previously from irradiating a different sample with a pulse of the light.

The foregoing and additional features and advantages of the invention will be more readily apparent from the following detailed description, which proceeds with reference to the accompanying drawings.

BRIEF DESCRIPTION OF THE DRAWINGS

FIG. 8 is an elevational view of certain features of a sample chamber of a third embodiment of a light-absorption measurement apparatus according to the invention.

DETAILED DESCRIPTION

In the embodiments and working examples discussed below, a photo-acoustic measurement apparatus is employed for measuring changes in light absorption by a sample optical component. The present invention is not to be construed as limited to apparatus or methods employing such devices or measurement techniques.

A suitable photo-acoustic measurement device comprises, for example, a microphone or piezo-electric transducer (generally termed herein a "photoacoustic transducer") attached to a sample holder. As a sample optical component is held by the sample holder, acoustic signals generated in the sample in response to receiving pulses of light are detected by the photoacoustic transducer. Each acoustic signal is produced from a volumetric change exhibited by the sample due to a temperature change of the sample caused by impingement of a pulse of light either on the sample or near the sample. The photoacoustic transducer converts the acoustic signals into corresponding electric signals. Data concerning the non-radiant transition of the sample material from exposure to light is obtained through analysis of the intensity, phase, and other characteristics of the electrical signals. The amplitude of the acoustic signals is normally proportional to the thermal energy imparted to the sample by the light pulse. The thermal energy imparted to the sample by a light pulse is a function of the amount of light in the pulse absorbed by the sample. Hence, the amount of light absorbed by the sample normally can be calculated from acoustic data. (For a detailed explanation of the applicable theory, reference is made to *J. Appl. Phys.* 47(1):64; *J. Appl. Phys.* 51(6):3343; and *Can. J. Phys.* 64:147.) According to this method, the resolution of the signals generated from exposure of the sample to high-intensity light can be increased, which provides increased measurement sensitivity.

First Embodiment

Figure 1A:
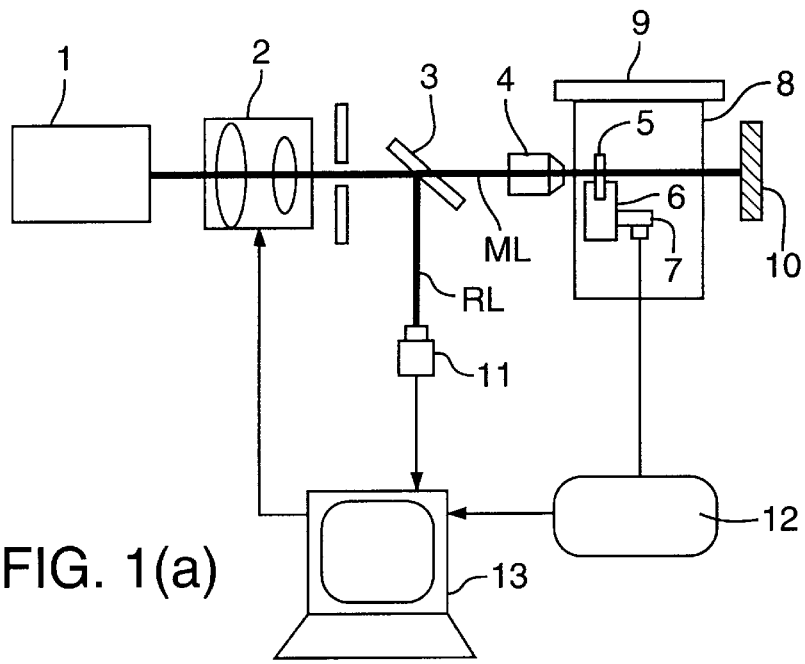
FIG. 1(a) is a schematic optical diagram of a first embodiment of a light-absorption measurement apparatus according to the invention.

A first embodiment of an apparatus (and associated method) for measuring changes in light absorption of a sample, according to the invention, is shown in FIG. 1(a). The FIG. 1(a) apparatus utilizes a photoacoustic transducer as summarized above. The FIG. 1(a) apparatus also utilizes a pulse laser to provide illumination light for the sample.

The FIG. 1(a) apparatus typically comprises a housing (not shown) containing a light-intensity-adjustment optical system 2 that adjusts the intensity of light produced by a high-intensity light source 1 (e.g., deep ultraviolet excimer laser). A beamsplitter 3 separates the intensity-adjusted laser light into a reference-light beam RL and a measurement-light beam ML. A condenser optical system 4 condenses the measurement-light beam ML onto a sample optical component ("sample") 5. A light-intensity sensor 11 receives the reference-light beam RL. The sample 5 is held by a sample holder 6 to which a photoacoustic transducer 7 (such as a piezoelectric acoustic sensor) is attached. A beam stopper 10 absorbs any measurement light ML passing through the sample 5.

Figure 1B:
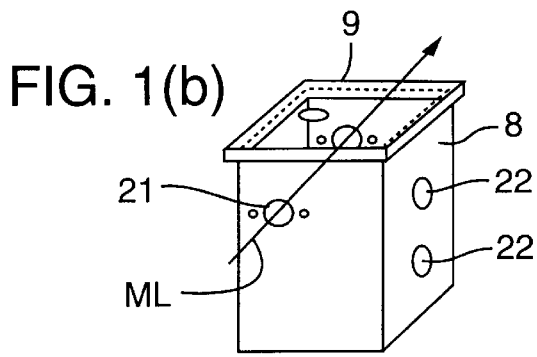
FIG. 1(b) is a schematic perspective view of a sample chamber as used in the FIG. 1(a) embodiment.

The sample holder 6 and photoacoustic transducer 7 are contained in a sample chamber 8. The sample chamber 8 includes a transparent window 21 (preferably made of quartz) that transmits the measurement-light beam ML as shown in FIG. 1(b). A gas-introduction tube (not shown, but described further in connection with the FIG. 3 embodiment) can be connected to a port 22 in the sample chamber 8. The gas-introduction tube is used to introduce into the sample chamber 8 a suitable gas for testing effects of adhesion and/or absorption of molecules of the gas by the sample 5.

Figure 2A:
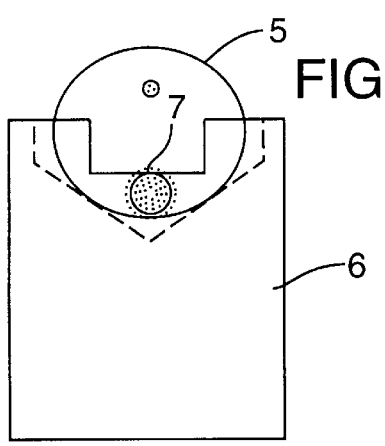
FIG. 2(a) is an elevational view of a sample optical component disposed on a sample holder including an acoustic sensor.
Figure 2B:
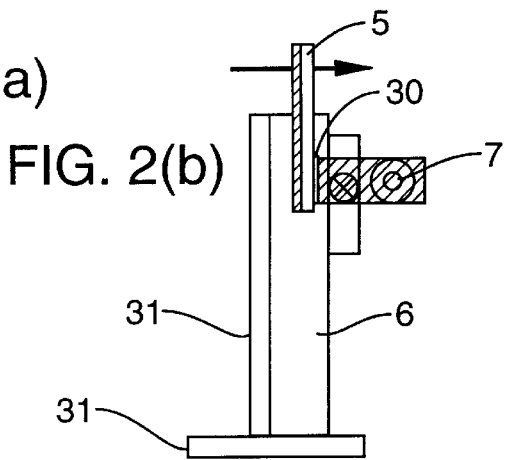
FIG. 2(b) is a vertical section of the sample holder of FIG. 2(a).

FIG. 2(a) depicts details of the sample holder 6 and sample 5. The sample holder 6 includes the photoacoustic transducer 7 situated so as to contact the sample 5 whenever the sample is mounted to the sample holder 6. Side elevational details are shown in FIG. 2(b).

The sample 5 is typically an optical component (e.g., glass or quartz) comprising a surficial coating such as a thin antireflective coating. The sample holder 6 is preferably made of a material having a low acoustic impedance. Actual contact of the sample 5 with the sample holder is preferably via a bridging material 30 that provides acoustic matching between the sample 5 and the sample holder 6.

Sensing of acoustic signals generated in the sample 5 is performed by the photoacoustic transducer 7. The acoustic sensor 7 is preferably mounted to the sample holder using an adhesive that provides stable acoustic matching between these components. Also, an amount of the bridging material 30 is placed between the photoacoustic transducer 7 and the sample 5.

A vibration-isolation material 31 (e.g., rubber sheeting or other suitable elastomeric material) is preferably mounted to the sample holder 6 at appropriate locations to provide acoustic isolation as required. The vibration-isolation material 31 helps block, for example, conduction of extraneous vibrations and acoustic noise from the external environment to the sample 5.

As light from the light source 1 passes through the light-intensity-adjustment optical system 2, the irradiation intensity of the light is adjusted as required to a desired level. The light is then separated into the reference-light beam RL and the measurement-light beam ML by the beamsplitter 3. The intensity of the reference-light beam RL (and thus of the light exiting the light-intensity-adjustment optical system 2) is monitored by the light-intensity sensor 11. The measurement-light beam ML is transmitted by the window 21 and irradiates the sample 5 disposed inside the sample chamber 8.

Figure 3:
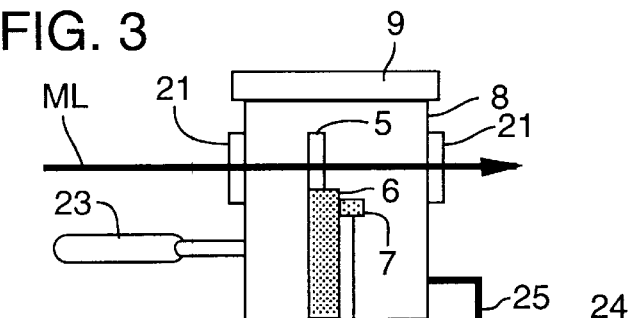
FIG. 3 is a schematic elevational section of the sample chamber of FIG. 1(b) connected to a source chamber containing a substance that can contribute gas molecules that can adhere to or be absorbed by a sample optical component in the sample chamber.

Inside the sample chamber 8, the sample 5 can be situated in an environment comprising molecules of a contaminant substance that can adhere to or be absorbed by the surface of the sample 5. As shown in FIG. 3, the environment inside the sample chamber 8 can be created by introducing into the sample chamber 8 molecules of any of various extraneous materials (e.g., organic materials or silicone materials) contributing contaminant molecules (e.g., organic molecules) that can adhere to and/or be absorbed by the surface of the sample 5.

To provide the sample chamber 8 with an environment including such extraneous molecules, a suitable "source material" (solid, liquid, or gas) can be introduced into a source chamber 24 from which molecules of the source material can be controllably transferred to the sample chamber 8 through a conduit 25. Preferably, the source material is placed in the source chamber 24 before the sample 5 is placed in the sample chamber 8. Molecules of the source material can be transferred from the source chamber 24 either with or without a carrier such as a carrier gas (e.g., air or nitrogen) or a carrier liquid. Thus, an environment is achieved in the sample chamber 8 favoring controlled adhesion and/or absorption of molecules of a desired source material to the surface of the sample 5.

Alternatively, the source material can be placed directly into the sample chamber 8.

Acoustic signals detected by the photoacoustic transducer 7 are routed to an FFT processor 12 that applies fast Fourier transform (FFT) methods to the signals to, inter alia, eliminate noise. The FFT processor 12 routes signals to a computer 13 that calculates the change in light absorption exhibited by the sample 5 with cumulative light exposure in the sample-chamber environment. Such changes are calculated from data concerning the intensity of the reference-light beam RL as monitored by the light-intensity sensor 11 and acoustic signals produced by the sample 5 when irradiated by pulses of the measurement-light beam ML. Generally, a change in amplitude of the acoustic signals produced by the sample 5 is proportional to a corresponding change in light absorption exhibited by the sample 5.

The computer 13 can include a display used for displaying the results of data processing performed by the computer 13. The computer 13 can also include a data-input device (e.g., a keyboard) allowing an operator to input data.

Because a large variation can exist in the amount of light irradiated with each pulse from a pulse laser, it is preferable to standardize the amount of light per pulse when comparing acoustic signals generated in response to the pulses. In other words, if the intensity of the acoustic signals is S and the amount of light irradiated per pulse is I, then a value proportional to S/I can be monitored. By continuously irradiating the reference-light beam RL, actual changes in light absorption by the sample are determined by monitoring changes in the S/I value.

If a gas is introduced into the sample chamber 8 to cause adhesion and/or absorption of molecules of a source material on the surface of the sample 5 inside the sample chamber 8, it preferable to quantitatively control the amount of gas flowing into the sample chamber 8. Such control allows the number of source-material molecules adhering to and/or absorbed by the surface of the sample 5 to be quantitatively compared and evaluated. To control the flow rate of a gas into the sample chamber, it is preferred that the conduit 25 be provided with a variable-pressure or variable-flowrate valve with a suitable monitor for the pressure or flowrate, respectively. These components are not shown in FIG. 3.

To evaluate the influence on changes in light absorption caused by adhesion or absorption of gaseous molecules of the source material introduced into the sample chamber 8, it is advantageous to measure the constituents of the gas introduced into the sample chamber 8 and the concentrations of the constituents in the gas. To such end, a device is preferably included with the FIG. 1(a) embodiment for separating and identifying components of the gas. Preferably, such a device is a GCMS (gas chromatograph/mass spectrometer), wherein the mass spectrometer is preferably a quadrupole type as known in the art. Referring to FIG. 3, gas can be collected, for analytical purposes, from the sample chamber 8 using a gas-collection vessel 23 (preferably comprising a porous material for absorbing the gas). Preferably, the gas is collected at a uniform flow rate and for a predetermined period of time. After collecting the gas, the gas-collection vessel 23 can be disconnected from the sample chamber 8 and transported for remote GCMS analysis if required.

Alternatively or in addition, sensing can be performed by permanently connecting suitable dedicated gas analyzers or monitors to the sample chamber 8. Examples of such analyzers or monitors include, but are not limited to, oxygen, nitrogen, and/or other gas monitor; and humidity sensor.

Gas introduced into the sample chamber 8 is not limited to only one gas. The sample chamber 8 can be fitted with multiple gas-introduction ports to allow a respective number of different types of gas to be simultaneously introduced into the sample chamber 8.

Changes in light absorption by the sample 5 can be measured while simultaneously introducing a gas into the sample chamber 8, particularly under situations in which molecules of the gas undergo a photochemical reaction with the light used to irradiate the sample 5. The products of such reactions can include one or more compounds that adhere to or are absorbed by the sample 5.

Performing measurements in such a way eliminates a serious problem with prior-art apparatus and methods in which the sample, after exposure to the gas in a sample chamber, must be left in the sample chamber with the gas for a period of time while the sample chamber is conveyed to a remote measurement device. During the time required to transport the sample chamber to the measurement device and to perform measurements of any changes of light absorption by the sample, the sample can undergo further reactions with the gas and thus experience changes that are difficult to control and evaluate.

When passing a pressurized gas through a conduit from a source to the sample chamber 8, unwanted sounds are typically generated at the terminus of the conduit (from which terminus gas enters the sample chamber 8) due to a "whistle" effect. Such sounds can be detected by the photoacoustic transducer 7 as noise as the photoacoustic transducer 7 is measuring photoacoustic signals generated in the sample 5. Such noise can be effectively reduced or eliminated by, for example, limiting the acoustic conductance of the conduit used to introduce the gas.

In reducing acoustic "noise" in the detected photoacoustic signals, it is usually not necessary to reduce the intensity of all extraneous sounds that could be transmitted to the sample 5. Rather, a certain frequency component of the photoacoustic signals from the sample 5 can be selected for measurement. It is desirable that the selected frequency component originate from inside the sample 5 rather than from an extraneous source such as a gas-introduction port during gas introduction. To facilitate such selection, it is preferred to provide a mechanism for shifting the frequency of sounds emanating from the gas-introduction port; such a mechanism can comprise, for example, a muffler for the gas-introduction port.

Second Embodiment

Figure 7:
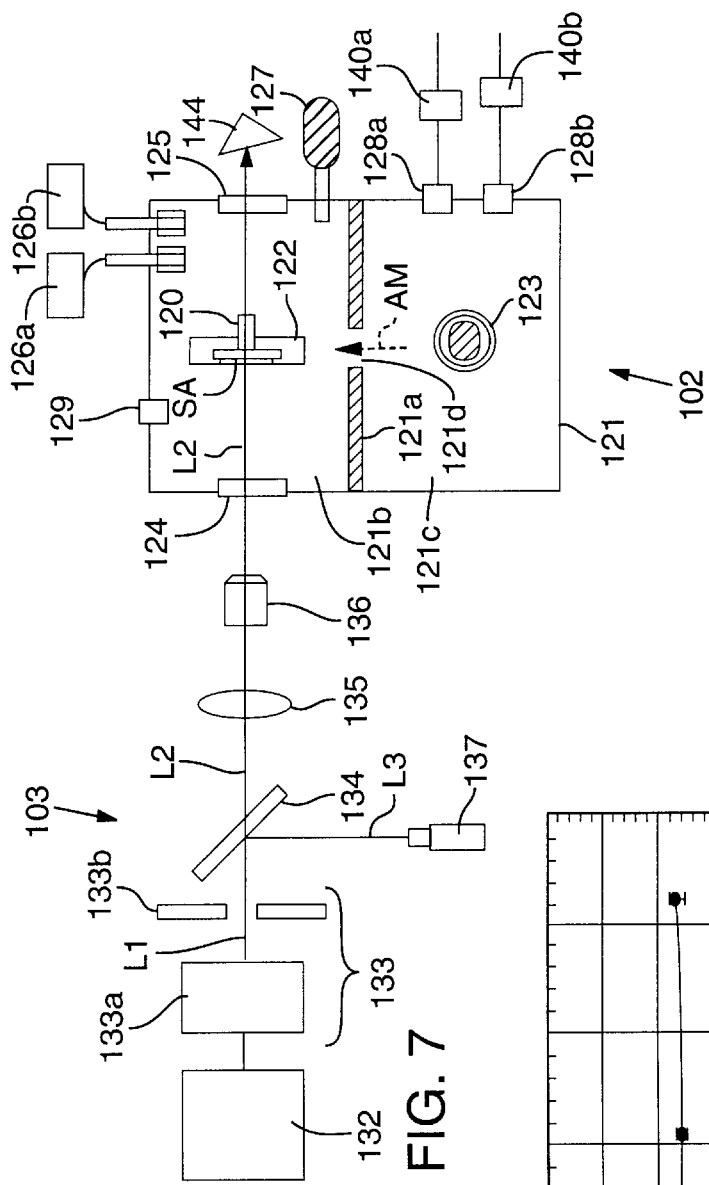
FIG. 7 is a schematic optical diagram of a second embodiment of a light-absorption measurement apparatus according to the invention.

This embodiment of an apparatus for measuring changes in light absorption of a sample optical component is depicted in FIG. 7. The FIG. 7 apparatus comprises a sample chamber 102 and an illumination system 103. The sample chamber 102 is typically a sealed housing configured so as to hold a sample SA in a controlled environment during testing. The illumination system 103 illuminates the sample SA inside the sample chamber 102.

The illumination system 103 comprises a light source 132 that generates a short-wavelength (e.g., ultraviolet) laser light beam L1 to which the sample SA may be sensitive. A light-intensity-adjustment optical system 133 is situated so as to receive the light beam L1 from the light source 132 and adjust and regulate the intensity of the light beam L1 such as by changing the diameter of the light beam L1. A beamsplitter 134 separates the light beam L1 exiting the light-intensity-adjustment optical system 133 into a measurement beam L2 and a reference beam L3. A relay lens 135 and an objective lens 136 condense the measurement beam L2 onto the sample optical component ("sample") SA. A reference-light sensor 37 measures the intensity of the reference beam L3.

The light source 132 can comprise any of various types of laser light sources, such as a CW (continuous wave) laser or pulse laser. Although the light beam L1 is typically in the ultraviolet region, the light beam L1 can be of a longer wavelength as desired or required.

The light-intensity-adjustment system 133 preferably comprises a zoom lens 133a that adjusts the diameter of the light beam L1 and the irradiation intensity of the measurement beam L2 impinging on the sample SA. The light-intensity-adjustment system 133 also preferably comprises an aperture 133b allowing the irradiation surface area of the measurement beam L2 on the sample SA to be adjusted.

The reference-light sensor 137 preferably comprises a bipolar photomultiplier configured and situated such that the reference beam L3 reflected by the beamsplitter 134 is incident on the reference-light sensor 137. Thus, the intensity of the measurement beam L2 is indirectly monitored and controlled by the reference-light sensor 137.

The sample chamber 102 comprises a housing 121 that contains a sample holder 122. The sample holder 122 is configured to retain the sample SA for testing. The sample chamber 102 also encloses a source 123 of an "adhesion gas" AG (i.e., a gas comprising molecules of an "adhesion material" AM (analogous to the "source material" discussed above) that can adhere to the surface of the sample SA and cause surficial fogging or clouding of the surface). The housing 121 preferably comprises two compartments: a sample compartment 121b enclosing the sample holder 122, and a source compartment 121c enclosing the adhesion-gas source 123. The two compartments are separated by a wall 121a defining an opening 121d.

A side of the sample compartment 121b is provided with an entrance window 124 (preferably made of quartz glass) that transmits the measurement beam L2 to the sample SA. On an opposing side of the sample compartment 121b is an exit window 125 (preferably made of quartz glass) that transmits the measurement beam L2 that has passed through the sample SA. A beamsplitter 144 is disposed adjacent the exit window 125.

Gas sensors 126a, 126b, as required, extend through a wall of the sample compartment 121b for measuring the concentrations of respective gases (for example, oxygen and water vapor) inside the sample compartment 121b in real time. A gas-collection vessel 127 (preferably made of quartz glass) extends through a wall of the sample compartment 121b for collecting molecules of one or more selected gases (for example, molecules of an organic compound or silicone compound) from the interior of the sample compartment 121b that are otherwise difficult to measure in real time. The gas-collection vessel 127 can include a gas-absorbent for collecting the desired molecules. A method such as GCMS can be used currently or at a later time to analyze the collected gas molecules.

Gas-introduction ports 128a, 128b as required extend through a wall of the source compartment 121c. The gas-introduction ports 128a, 128b are preferably made of an inert material such as a fluoride resin. The gas-introduction ports 128a, 128b are separately connected to respective gas sources (not shown) for introducing gases (e.g., a carrier gas) as required into the source compartment 121c. The amounts of adhesion gas AG and carrier gas thus released into the source compartment 121b are preferably controlled by flow regulators 140a, 140b.

A gas-discharge outlet 129 extends through a wall of the sample compartment 121b. The gas-discharge outlet discharges gas (such as molecules of the adhesion gas AG and carrier gas), previously introduced into the sample compartment 121b from the source compartment 121c, to the outside of the housing 121.

The housing 121 is preferably formed from a type of stainless steel that does not generate any molecules of the adhesion gas AG and that otherwise does not cause surficial clouding of the sample SA. As an alternative to stainless steel, the housing 121 can be formed from any of various other materials (for example, aluminum) that exhibit very low degassing. A housing 121 made in such a way allows the atmosphere inside to be rigorously controlled so as to allow accurate determinations to made of the effects of, for example, the adhesion gas on changes in light absorption of the sample SA. By exhibiting reduced degassing, such a housing also effectively removes what has otherwise (in conventional apparatus) been a source of noise when conducting evaluations of gases in the housing, even if the detected gases are not the gases that are directly responsible for surficial clouding of the sample SA. Hence, the housing 121 is preferably made of a material exhibiting a sufficiently low degassing level so as not to affect the accuracy of measurements of the gases inside the housing 121. Thus, materials such as brass, that normally exhibit substantial degassing, should not be used to fabricate either the housing 121 or any component situated inside the housing. Even desirable materials, such as aluminum or stainless steel, should be sufficiently cleaned and heated beforehand to drive off entrapped gas molecules.

The sample SA can be, for example, an optical flat coated with an anti-reflective coating formed as an optical thin film on the surfaces of the flat. To introduce the sample SA into the housing 121, the housing 121 preferably defines an opening (normally covered by a sealable door or other suitable cover; not shown) for inserting and removing the sample SA from the sample compartment 121b. The cover is preferably sealed around the opening using a fluoride resin (Teflon) seal.

The sample holder 122 is preferably formed from a fluoride resin (Teflon) or other suitable material exhibiting minimal degassing and a comparatively large acoustic impedance. The sample holder 122 is preferably thoroughly cleaned, before placement inside the sample compartment 121b, to prevent unwanted contamination of the sample compartment 121b and excessive extrinsic noise from being transmitted to the sample SA during acoustic measurements.

A photoacoustic transducer 120 (comprising, for example, a piezoelectric element) is adhered to the rear surface of the sample SA in a manner allowing acoustic waves from the sample SA to be efficiently transferred to the photoacoustic transducer 20. The photoacoustic transducer 20 detects photoacoustic signals generated by the sample SA. A photoacoustic signals is generated from an instantaneous change in the volume of the sample SA whenever the sample SA is illuminated with a pulse of intense light irradiation from the measurement beam L2. Changes in the photoacoustic signals observed after a number of pulses are substantially proportional to respective changes in absorption by the sample SA of light from the measurement beam L2. Hence, it is possible, with this example embodiment, to measure and monitor the appearance of clouding on the surface of the sample SA as well as any changes in the clouding condition accompanied by fluctuations in the photoacoustic signals.

The adhesion-gas source (source material) 123 can be, for example, a mass of an adhesive agent for optical components. In any event, the adhesion-gas source 123 functions as a source of a corresponding adhesion gas AG that can be deposited on or absorbed by the surface of the sample SA in a manner that results in clouding of the surface. The adhesion-gas source 123 can be changed as required to study the effects of different source materials on sample clouding.

In other words, because the relationship between each of various types of adhesion gas AG and clouding can be separately evaluated quantitatively, changes in light absorption exhibited by the sample SA can be measured while changing the adhesion gas AG.

Whenever the adhesion gas AG is supplied from an adhesion-gas source 123 placed inside the supply compartment 121c, it is not necessary to supply the adhesion gas AG from the gas-introduction ports 128a, 128b. In such instances, the gas-introduction ports 128a, 128b and the gas-discharge outlet 129 can be closed. Alternatively, the adhesion gas AG can be supplied through one or more of the gas-introduction ports 128a, 128b, in which instance an adhesion-gas source 123 (i.e., an adhesion material AM, synonymous with the "source material" discussed above) is not placed in the source compartment 121c.

Operation of the FIG. 7 apparatus is as follows: The sample optical component SA is placed inside the sample compartment 121b of the housing 121. At this time, the gas sensors 126a, 126b and the gas-collection vessel 127 are used to confirm that the atmosphere inside the sample compartment 121b is not contaminated. In order to produce a desired atmosphere inside the sample compartment 121b, an adhesion-gas source 123 (that generates the adhesion gas AG) can be placed in the supply compartment 121c. At the same time, monitoring of the atmosphere inside the sample compartment 121b is begun using the gas sensors 126a, 126b.

Simultaneously with or instead of placing an adhesion-gas source 123 in the supply compartment 121c, a carrier gas (containing an adhesion gas AG) can be introduced into the sample compartment 121b using the gas-introduction ports 128a, 128. The gas introduced using the gas-introduction ports 128a, 128b is not limited to one type. Any of various gases can be introduced.

To more accurately control the atmosphere inside the sample compartment 121b, a suitable carrier gas can be introduced from, for example, the gas-introduction port 128a.

Pulses of the measurement beam L2 from the illumination system 103 pass through the entrance window 124 and are incident on the sample SA while acoustic signals generated in the sample SA are monitored by the photoacoustic transducer 120.

The amplitude of the signals produced by the photoacoustic transducer 120 increases as light absorption of the sample SA increases due to correspondingly increasing surficial clouding of the sample. Therefore, progressive degradation of the performance of the sample optical component due to clouding in the presence of a particular type and concentration of adhesion gas AG can be quantitatively evaluated and monitored.

By minimizing the amount of degassing from the inner surface of the housing 121 during such an evaluation, the amount of adhesion gas AG supplied to the surface of the sample SA can be precisely controlled. This minimizes background noise while allowing changes in light absorption of the sample to be accurately determined.

The photoacoustic transducer 120 allows changes in light absorption to be detected without removing the sample SA from the housing 121 Hence, variations in the irradiation position on the sample SA can be eliminated. Also, changes in physical properties of the sample during transport and storage from a separate container to the housing 121 and from the housing 121 to a separate measurement device are greatly minimized, allowing measurements of locations where adhesion and absorption occur using a simple device.

With respect to this embodiment, measurements of the effects of surficial clouding can be made not only by introducing an adhesion gas AG into the housing 121 but also by using intermittent (pulsed) irradiation of a sample in an atmosphere containing an adhesion gas, wherein adhesion and absorption of molecules of the gas occur following the irradiation.

After use for obtaining measurements of the effects of clouding by a specific adhesion gas on changes in absorption of the sample, it is preferable to replace the housing 121 before studying the effect of a different adhesion gas. Such a practice eliminates any effects of residual adhesion gas (e.g., adhering to the interior walls of the housing 121) in the housing 121. To such end, multiple otherwise identical housings 121 can be made available and a new housing used whenever the adhesion gas is changed.

In a working example of this embodiment, the optical component sample SA was a circular quartz glass flat (transmissive to the measurement-light beam L2) having a thickness of 2 mm, a diameter of 30 mm, and a surficial thin-film coating of 1 μm maximal thickness.

The light source 132 was a KrF excimer laser ($\lambda$=248 nm) with a pulse width of approximately 20 ns. The beam diameter of the measurement beam L2 on the surface of the sample SA was approximately 2 mm and the irradiation power was approximately 10 mJ/cm$^2$.

The sample SA and sample holder 122 were contained in a stainless steel housing 121 in which the atmosphere included a small amount of adhesion gas of known concentration. Measurements were also conducted with the sample SA and sample holder 122 being contained in a separately provided aluminum housing 121. The housing 121 included a sealable cover. Before use, the housing 121 was cleaned using an alkali cleaner, rinsed with water and allowed to dry. Afterward, the housing 121 was dried in an electric oven (ca. 90° C.).

A Si-based adhesive (silicone adhesive) was placed in the source compartment 121c as an adhesion-gas source 123.

A zirconia type oxygen sensor and a polymer-based thin-film type hygrometer extended through a wall of the housing 121 as the gas sensors 126a, 126b. A gas-collection vessel 127 also extended through a wall of the housing. The gas-collection vessel 127 contained a gas absorbent for later analysis of adhered molecules by GCMS. These features allowed a distinction to be made of the adhesion gas (almost entirely a silicone compound) from the adhesion gas produced by the adhesion-gas source 123.

Acoustic signals generated in the sample SA were detected by a photoacoustic transducer 120 in which an aluminum receiving plate was mounted to a PZT (lead zirconate titanate) piezoelectric element. The photoacoustic transducer 120 was attached to the rear surface of the sample SA using a high-vacuum grease exhibiting very low outgassing. Before use, the photoacoustic transducer 120 was cleaned using an alkali cleaner, rinsed with water, and steam-dried using a wet-process cleaning device such as a type used in cleaning semiconductor devices. The photoacoustic transducer 120 was then secured to the rear surface of the sample SA.

The output voltage of the signal produced by the photoacoustic transducer 120 was measured as the measurement beam L2 irradiated the sample SA Photoacoustic signals generated in the sample due to absorption of pulses of the incident measurement light by the sample occurred approximately 8 μsec after each pulse of measurement light L2. The signals from the photoacoustic transducer 120 were suitably filtered to remove electromagnetic noise and oscillation.

In this example, the main acoustic frequency was approximately 150 kHz. After selecting a wavelength close to this frequency using a low-pass filter and a high-pass filter, the analysis was carried out by fast Fourier transform (FFT) methods.

As the sample SA was repeatedly exposed to pulses of measurement light, photoacoustic signals generated in the sample (corresponding to changes in the amount of light absorbed by the sample) were monitored as a function of cumulative light exposure (number of pulses). Observed changes in the photoacoustic signals were due to a change in the sample SA caused by a combination of light irradiation onto the sample and absorption and adhesion to the sample of molecules of adhesion gas from such molecules provided by the adhesion-gas source 123 to the atmosphere inside the housing 121. Measurements were also performed without an adhesion-gas source 123 placed inside the housing 121. In such an instance, variations in the acoustic signals generated by the sample were not observed.

As a control, the amount of degassing from the housing 121 was evaluated (after cleaning but prior to use). Degassed molecules were collected and analyzed by GCMS. With a stainless steel housing 121, housing degassing contributed no more than $1/10^4$ to the overall amount of adhered/absorbed gas. Similar results were observed with an aluminum housing 121. These results were favorable for quantitative determinations of the effects of adhesion gas (released from the adhesion-gas source 123) on light absorption by the sample SA.

Third Embodiment

A sample chamber 202 according to this embodiment is depicted in FIG. 8, which represents a modification of the sample chamber 102 of the second embodiment.

The sample chamber 202 comprises a housing 221 defining an opening 221e for inserting and removing an optical component sample SA. The opening 221e is covered using a sealing cover 221f (preferably made of glass). The cover 221f is secured to the rim of the opening 221e using a fluoride resin (Teflon) sealant. The inner surface of the housing 221 is covered with an aluminum lining 250. The housing 221 encloses a sample holder 222 that is also covered with the aluminum lining 250. A photoacoustic transducer 220 is attached to the sample holder 222 and is also covered with the aluminum lining 250. The sample SA is mounted to the sample holder and is contacted by the photoacoustic transducer 220.

The housing 221 comprises first and second windows 224, 225, respectively, and first and second gas-introduction ports 228a, 228b, respectively.

An "adhesion gas" AG generated by a source material 223 can adhere to the inner surfaces of the housing 221 as well as to the surface of the sample SA. Thus, it is possible that residual adhesion gas from a previous measurement can adversely affect subsequent measurements of light absorption by a sample SA. Thus, in this embodiment, the aluminum lining 250 is preferably replaced after every measurement. This practice increases the level of cleanliness of the housing 221, thereby providing more accurate measurements of variations in light absorption by the sample compared to a scheme in which the housing 221 is simply cleaned after each measurement.

The amount of actual degassing by the housing 221 was measured in a situation in which the aluminum lining 250 is mounted in the housing 221 after cleaning the aluminum lining 250 in an organic solvent. Degassing was monitored by GCMS. Results indicated that, if an a source material 223 was not placed in the housing 221, the amount of degassing remained at a low level that did not interfere with light-absorption measurements of the sample SA.

Measurements of the effects of sample clouding can be performed, using the third embodiment, in a manner similar to that described above for the second embodiment. Actual results are similar to results obtained with the second embodiment. After measurements were performed of the effects of clouding (from adhesion gas generated by the source material 223, and wherein the housing 221 included the aluminum lining 250), no changes were observed in degassing, relative to initial levels of degassing, whenever the aluminum lining 250 and the source material 223 were removed from the housing 221 after each measurement.

In contrast, if the source material 223 were placed in the housing 221 and clouding measurements were performed without the aluminum lining 250 being present in the housing 221, degassing from the inner surface of the housing 221 was about $10^3$ times the degassing observed initially. These results indicated that, by providing a lining to the housing 221 such as the aluminum lining 250, residual substances can be removed from the sample chamber 102 that would otherwise interfere with the accuracy of the light-absorption measurements.

In the second and third embodiments described above, photoacoustic signals are detected that correspond to the amount of light absorbed by the sample SA, as a function of the degree to which the surface of the sample SA has become clouded by deposition of molecules of an adhesion gas. However, a photoelectric transducer can be used to measure the amount of light scattered from the sample SA, which can also yield data useful for measuring the degree of clouding of the sample.

Fourth Embodiment

Figure 9:
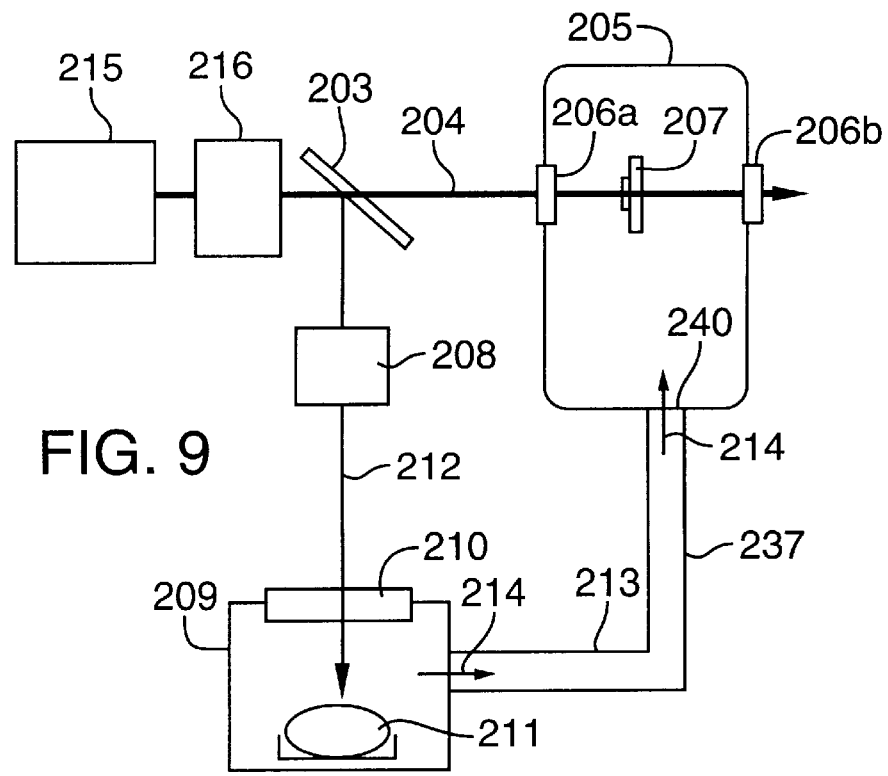
FIG. 9 is a schematic optical diagram of a fourth embodiment of a light-absorption measurement apparatus according to the invention, in which divergent light split from the sample-irradiating light is used to irradiate the source material.

An apparatus for measuring a change in light absorption according to this embodiment is shown in FIG. 9. In the FIG. 9 embodiment, the atmosphere in which an optical component sample 207 is placed can be controlled. In other words, the sample 207 is placed inside a sealable sample chamber 205 in which the atmosphere can be controlled. The sample chamber 205 includes a first light-transmitting window 206a. Measurement light 204 is irradiated onto the sample 207 so as to ascertain the effects of cumulative exposure of the sample to the measurement light, particularly as the sample is simultaneously exposed to a specific gas or gas mixture.

To supply at least a portion of the gas, a source material 211 (typically a liquid or solid) is placed inside a source chamber 209. The source material 211 serves as a source of gas molecules known or suspected of being able to adhere and/or absorb to the surface of the sample 207. Such gas can be supplied from the source chamber 209 to the sample chamber 205 through a conduit 237 interconnecting the two chambers. The conduit 237 opens into the sample chamber 205 via an inlet 240 used for discharge of the gas into, and exhaust of gas from, the sample chamber 205. The gas passing through the inlet 240 into the sample chamber 205 can be mixed with a carrier gas such as air or nitrogen so as to create a desired atmosphere inside the sample chamber 205.

The gaseous environment created in the sample chamber 205 can be a mixture of various gases other than the gas produced by the source material 211 and carrier gas. To such end, the sample chamber 205 can be provided with multiple gas inlets (not shown) for simultaneously introducing any of various gases. Such gas inlets can also be used to introduce diluent or carrier gases.

The source material 211 in the source chamber 209 is preferably irradiated, typically simultaneously with the sample 207. To such end, the source chamber 209 preferably includes a window 210 that transmits a light beam 212 of a specified wavelength into the source chamber 209 to irradiate the source material 211. The light beam 212 preferably has a wavelength selected for its possible role in forming a gas, from the source material 211, that can adhere to or be absorbed by the surface of the sample 207 and thus cloud the sample 207.

The light beam 212 is produced by a light source 215 (e.g., an excimer laser). The light produced by the light source 215 passes through a light-intensity-adjustment system 216 to a beamsplitter 203. Light 212 reflected from the beamsplitter 203 passes through the window 210 to the source material 211. Light 204 passing through the beamsplitter 203 passes through a first window 206a in the sample chamber 205.

The light 212 actually irradiating the source material 211 preferably exhibits some degree of scattering so as also to irradiate around the periphery of the source material 211. The light 204 irradiating the sample 207 also preferably exhibits such scattering. The scattering can be generated by directly scattering light from, for example, an optical-element sensor or by reflection.

The source material 211 preferably comprises a substance ("source material") that, when irradiated with light, generates a gas comprising molecules that can adhere to or be absorbed by the surface of the sample 207. For example, the source material can be in the form of a coating that, when irradiated, produces a gas or finely particulate matter that can adhere to or be absorbed by the surface of the sample 207.

The configuration shown in FIG. 9 permits the light 204, produced by the light source 215, irradiating the sample 207 to have the same wavelength as the light 212, produced by the same light source 215, used to irradiate the source material 211. The light 212 directed toward the source material 211 preferably passes through a light-intensity controller 208 that controls the intensity of the light 212, taking into consideration factors such as the actual intensity of the scattered light.

Fifth Embodiment

Figure 10:
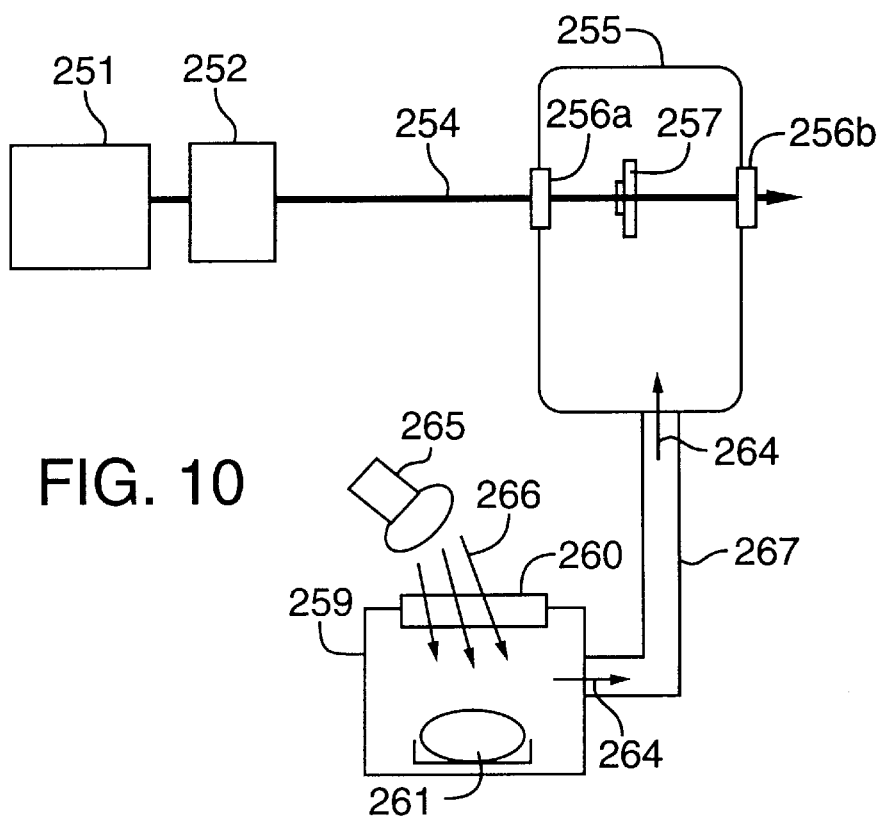
FIG. 10 is a schematic optical diagram of a fifth embodiment of a light-absorption measurement apparatus according to the invention, in which light from an ultraviolet lamp (separate from the sample-irradiating light) is used to irradiate the sample.

This embodiment, shown in FIG. 10, allows high-energy or high-intensity light to be irradiated onto a source material situated in the vicinity of an optical component sample that is undergoing, by light irradiation, an optical cleaning process. The sample-irradiation light is preferably ultraviolet produced by a high-pressure mercury lamp or excimer laser. Impingement of the sample-irradiation light onto the surface of the sample removes surficial contamination by facilitating a photochemical reaction. Oxygen is preferably introduced while the sample is being irradiated as required to facilitate the photochemical reaction.

During optical cleaning of an optical component, molecules can be generated that adhere to and/or are absorbed by the sample optical component due to irradiation of extraneous materials (such as a seal material inside the chamber in which such optical cleaning is conducted or an adhesive used to bond separate optical elements together). The FIG. 10 apparatus is particularly adapted for examining such phenomena and for evaluating the source of molecules that adhere to or are absorbed by the sample during optical cleaning.

The FIG. 10 apparatus comprises a sample chamber 255 comprising first and second light-transmissive windows 256a, 256b and adapted to contain an optical-component sample 257. A source chamber 259 is connected to the sample chamber 255 via a conduit 267. The source chamber 259 comprises a light-transmissive window 260 and is adapted to contain a source material 261 (i.e., a source of molecules that can adhere to or be absorbed by the sample 257).

The FIG. 10 apparatus also comprises an illumination light source 251 and a separate ultraviolet lamp 265. Light 266 from the ultraviolet lamp 265 passes through the window 260 and irradiates the source material 261. Such irradiation causes photochemical breakdown of the source material 261 which generates a gas containing molecules that can adhere to or be absorbed by the sample 257. The gas passes (arrows 264) through the conduit 267 into the sample chamber 255 where molecules of the gas adhere to and/or are absorbed by the sample 257. Any such adhesion and/or absorption is detected as a change in absorption by the sample 257 of the illumination light 254.

The FIG. 10 apparatus also includes a light-intensity-adjustment optical system 252 that controls the intensity of the irradiation light 254.

Sixth Embodiment

When irradiating light onto a source material in order to study the release from the source material of molecules that could adhere to or be absorbed by an optical component sample, it is preferred to minimize the amount of extraneous light (such as scattered light) impinging upon the source material. In other words, light scattered from light irradiated onto an optical component sample is preferably prevented from irradiating any other material (such as the source material) that could supply molecules that can adhere to and/or be absorbed by the sample. The fourth and fifth embodiments are particularly suitable for such purposes because the source material is retained in a chamber (source chamber) that is separate from the sample chamber.

Figure 11:
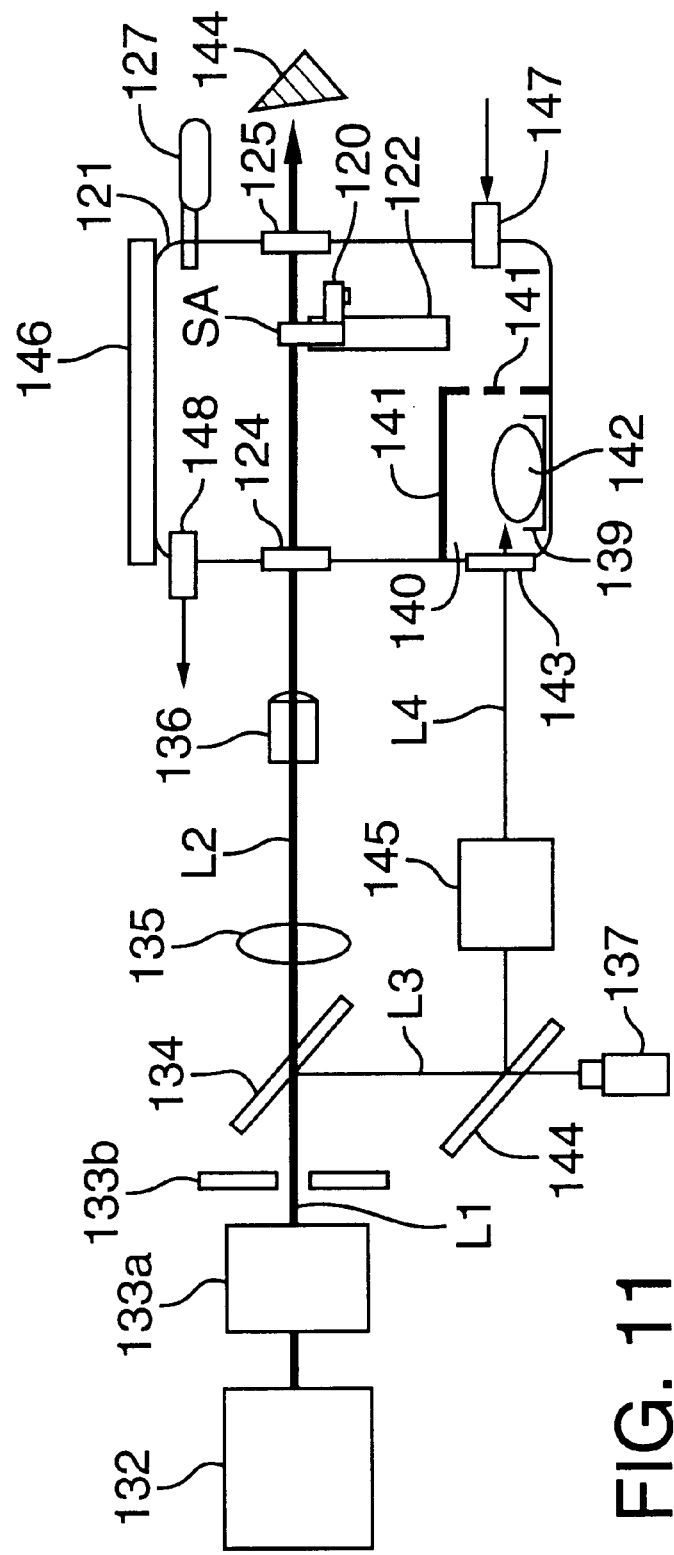
FIG. 11 is a schematic optical diagram of a light-absorption measurement apparatus as used in Working Example 4 and usable, with slight modification, in Working Examples 5 and 6.

The sixth embodiment also satisfies such criteria by comprising a chamber divided into two portions, one for the sample and a separate chamber for the source material. The sixth embodiment is shown in FIG. 11, in which components that are the same as in FIG. 7 have the same reference numerals and are not described further. Briefly, the components are: a light source 132, a zoom lens 133a, an aperture 133b, a beamsplitter 134, a relay lens 135, an objective lens 136, a reference-light sensor 137, a chamber 121, a sample holder 122 (which holds the optical component sample SA), an entrance window 124, an exit window 125, and a gas-collection tube 127.

The chamber 121 includes a sub-chamber 140 defined by a partition 141. A source material 142 is placed in the sub-chamber 140. The partition 141 defines apertures through which molecules, that can adhere to or be absorbed by the sample SA, can move to gain access to the sample SA. The sub-chamber 140 is provided with a window 143. Some of the reference light L3 reflected from the beamsplitter 134 passes through a second beamsplitter 144 to the reference-light sensor 137. The remaining reference light L4 is reflected by the second beamsplitter 144, passes through an intensity-adjusting optical system 145, passes through the window 143, and irradiates the source material 142. The partition 141 prevents the measurement light L2, irradiating the sample SA, from also irradiating the source material 142. Similarly, the partition 141 prevents the light L4, irradiating the source material 142, from also irradiating the sample SA.

The chamber 121 also includes a sealable cover 146, a gas-inlet port 147 as required, and an exhaust port 148.

Seventh Embodiment

In the sixth embodiment (as well as the fourth and fifth embodiments), the sample SA (FIG. 11) is irradiated while being exposed to an atmosphere comprising gas molecules that can adhere to and/or be absorbed by the sample. Such a procedure is preferred. If the sample SA otherwise had to be removed from the sample chamber to a different environment for measurements of light absorption, it would be difficult to establish (when performing the measurements) a proper location on the sample at which to perform the measurements (relative to the location on the sample SA irradiated by the light L2. It would also be necessary, when evaluating the results of such remotely made measurements, to consider changes in the physical properties of the sample SA during transport from the chamber 121 to the remote measurement location.

Moreover, using a conventional photoelectric transducer for measuring changes in the optical properties of the sample SA caused by adhesion and/or absorption of molecules can require very complicated detection and analysis circuitry, with consequent loss of sensitivity. Another problem is the need to provide separate light sources for optical measurements of the sample and for irradiation of the sample, with consequent high cost.

As described above, short-wavelength light, such as ultraviolet light, normally has a large photon energy that can interact with many substances. As a result, when an optical component sample is irradiated on its front surface, small amounts of adhered and/or absorbed extraneous material on the rear surface of the sample can substantially affect the amount of light absorbed by the sample. Therefore, measurements of the amount of light absorbed by the sample can provide an excellent measure of the degree to which the extraneous material has adhered to or been absorbed by the sample.

Referring further to FIG. 11, the photoacoustic transducer 120 can be a microphone or piezoelectric transducer attached to the sample holder 122. The photoacoustic transducer 120 detects and converts acoustic sounds, generated in the sample SA due to volumetric changes in the sample arising from rapid heating and cooling of the sample as the sample receives a light pulse, to corresponding electric signals. Such heating and cooling occurs with each pulse of irradiation light L2 on the sample SA. Various information related to non-radiant transition of the sample can be obtained through analysis of the amplitude, phase, and other characteristics of the electrical signals. The magnitude of the acoustic signals is normally proportional to the instantaneous thermal energy of the sample as it receives the light pulse and thus to the amount of light of the pulse absorbed by the sample. As a result, the amount of light absorbed by the sample can normally be determined from the acoustic signals. This theory is explained in *J. Appl. Phys.* 47(1):64; *J. Appl. Phys.* 51(6):3343, and *Can. J. Phys.* 64:147, all of which are incorporated herein by reference. This embodiment substantially increases the sensitivity of this method.

The amount of light absorbed by a sample irradiated by a pulse of intense pulsatile light (generated by a pulse laser or by chopping of a continuous-wave laser light) is obtained from a relationship between the irradiation intensity of the light pulse and the respective acoustic signals generated in the sample in response to the light pulse. (I.e., the amount of light absorbed by the sample is proportional to the amplitude of the acoustic signals generated by the sample.)

The amount of light produced per pulse from a pulse laser can vary considerably from one pulse to the next. Therefore, it is preferred, when analyzing the acoustic signals, to standardize the signals produced from each specific pulse to the amount of light irradiated on the sample during the respective pulse. For example, if the magnitude of the acoustic signal is denoted S and the amount of light irradiated on the sample during the respective pulse is I (both S and I not including any noise), a value proportional to S/I can be monitored. Any change in this value with repeated light pulses can be monitored to determine the amount by which light absorption changes with respect to a corresponding change in irradiation intensity. If the value of S/I exhibits an increase, then the amount by which light absorption changes from one pulse to the next can be regarded as having correspondingly increased; conversely, if the value of S/I exhibits a decrease, then the amount by which light absorption changes from one pulse to the next can be regarded as having correspondingly decreased.

Eighth Embodiment

It can be important to clarify the origin of any molecular absorption by and/or adhesion to the sample resulting from light irradiation. Such analysis can provide insight into the types and concentrations of compounds that could cause such absorption and adhesion. This embodiment is directed, inter alia, to means for detecting such phenomena.

The embodiments of FIGS. 9, 10, and 11 utilize a mass analyzer, such as a GCMS, to separate and identify compounds present in the adhesion gas and the concentration of the compounds. To collect molecules of the gas, a gas-collection vessel 127 (FIG. 11) is preferably used that contains as porous gas-scavenging, gas-attracting, or gas-absorbing material. After the gas-collection vessel 127 has collected gas molecules for a desired amount of time at a particular gas flowrate, the gas-collection vessel can be disconnected from the housing 121 and transported to a remote location for mass analysis of the collected gas. As discussed above, the gas-collection vessel 127 can be used to collect gas molecules while the sample is being irradiated, while the source material is being irradiated, or both.

If the subject of gas monitoring is a single gas compound, monitoring can alternatively be performed using a gas-specific sensor (if such a sensor is available for the specific gas) attached to the sample chamber. For example, oxygen in the sample chamber can be monitored using an oxygen sensor, and water vapor can be monitored using a humidity sensor.

In this embodiment, as in the fourth, fifth, sixth, and seventh embodiments, the optical component sample can be either coated (e.g., multilayer antireflection coating) or not coated. Furthermore, the sample can be an actual optical component or a representative portion of an optical component.

Ninth Embodiment

Figure 13A:
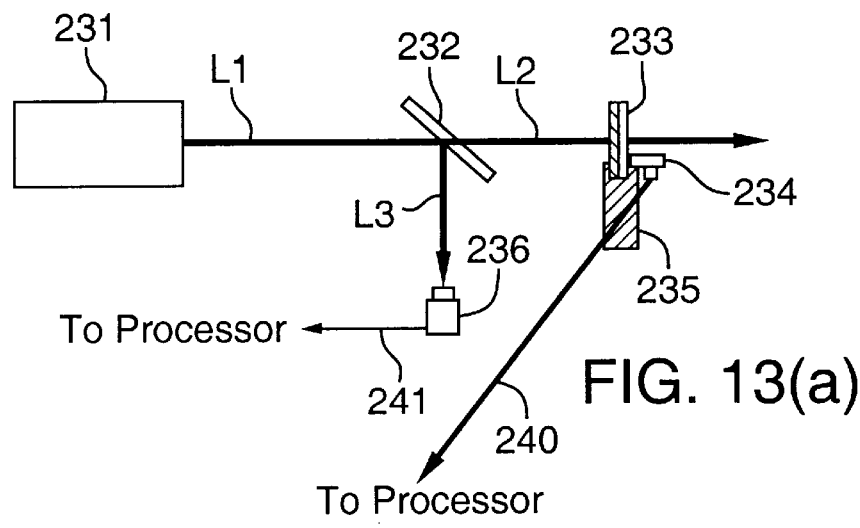
FIG. 13(a) is a schematic optical diagram of a photoacoustic-signal-measurement device as used in the ninth embodiment of a light-absorption measurement apparatus according to the invention.
Figure 13B:
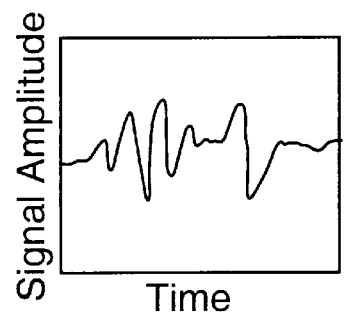
FIG. 13(b) is a representative acoustic signal (versus time) produced by the FIG. 13(a) device.
Figure 13C:
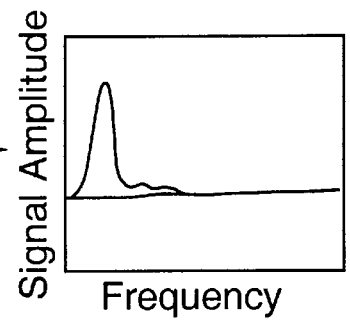
FIG. 13(c) is a representative acoustic signal (versus frequency) produced by the FIG. 13(a) device and corresponding to the signal shown in FIG. 13(b).

This embodiment is shown in FIG. 13(*a*), depicting a light source 231 that produces a light beam L1. A first portion L2 of the light beam L1 passes through a beamsplitter 232 to be incident on a sample 233. A second portion L3 of the light beam L1 is reflected by the beamsplitter 232 so as to be monitored by a light-intensity sensor 236. The light-intensity sensor 236 produces an electronic signal having an amplitude that is proportional to the intensity of the light L3.

The sample 233 is typically a glass or quartz optical element coated with a thin film (e.g., multi-layer antireflection coating). The sample 233 is mounted in a sample holder 235 formed from a material having a low acoustic impedance (e.g., Bakelite®). A photoacoustic transducer 234 (e.g., a piezoelectric element) serves to detect acoustic signals generated in the sample 233 whenever the sample receives a pulse of the light L2. The photoacoustic transducer 234 contacts the sample 233 via a suitable material (not shown) having an acoustic impedance substantially the same as the sample. An electronic signal 240 is thus produced by the photoacoustic transducer 234 in which noise is eliminated as much as possible. The electronic signal is routed to a frequency analyzer such as an FFT processor (not shown).

The amount of light L2 absorbed by the sample 233 is obtained from a relationship between the intensity of the light irradiated on the sample (as detected by the light-intensity detector 236 which produces the intensity signal 241) and the amplitude of the respective electronic signal 240. (Normally, the amount of light absorbed by the sample is proportional to the amplitude of the electronic signals 240.) Because there is normally a substantial variation in the intensity of the light L1 per pulse generated by the light source 231, it is preferred to standardize the signal 240 when comparing signals from different pulses. If the amplitude of a signal 240 is S and the intensity of a corresponding pulse of the irradiation light L2 is I (disregarding noise), then a variable proportional to S/I can be monitored and used to determine the change in light absorption by the sample as the sample is irradiated by successive pulses of light.

Variations in the amount of absorbed light by a sample and variations in the amount of light absorbed on a surface of the sample exert different effects on the waveforms of their respective acoustic signals. The method described below is used to separate these variations from each other for independent evaluation.

First, the time axis of each acoustic signal is separated into frequency components. Such separation allows noise components (electromagnetic noise that appears readily at higher frequencies and mechanical noise that appears readily at lower frequencies) to be eliminated.

It has been discovered that, during measurements performed on samples having a surficial light-absorbing thin-film layer, if variations are detected in the amount of light absorbed on the surface due to photo-degradation of the thin film or due to surface contamination of the thin film, then changes in the amplitudes of the main frequency components (frequency components of maximum amplitude) close to the resonant frequency of the measurement system (sample, holder, piezoelectric element) can be observed as an index of the frequency components. Whenever variations are observed in the amount of light absorbed on an optical component due to degradation of a thin film (if present) or to surface contamination, variations in the frequency components that are different from the main frequency components are observed.

If the amplitudes of frequency components due to surficial light absorption and for more depthwise light absorption in the sample are the same, then such components tend to be repeatable. As a result, frequency components originating from variations in amplitude can be examined in advance by performing measurements using a sample having a known light-absorption behavior. If the magnitudes of such components are plotted, variations in the amount of light absorption by both the sample itself and the surficial coating can be measured. This also makes it possible to readily automate the measurement operations.

Such methods are effective for readily distinguishing whether variations in light absorption by a sample are occurring on the surface of the sample or in locations within the thickness dimension of the sample. Such methods are especially effective for ascertaining whether degradation of the sample is occurring with repeated irradiation or for finding the energy of degradation occurring on the surface of the sample.

Working Example 1

The apparatus used to perform this working example is shown in FIG. 1 and described in the first embodiment. The light source 1 is a KrF excimer laser producing pulsatile light having a wavelength of 248 nm and a pulse width of 20 nsec. The optical component sample 5 is quartz glass with a thickness of 2 mm and a diameter of 30 mm. The sample 5 has a surficial multi-layer reflective film on one side thereof. The coating comprises alternating layers of $HfO_2$ and $SiO_2$.

The sample 5 is mounted in the sample holder 6 inside a stainless steel sample chamber 8. The sample chamber 8 is sealed using a Teflon seal and a glass cover 9.

Figure 4:
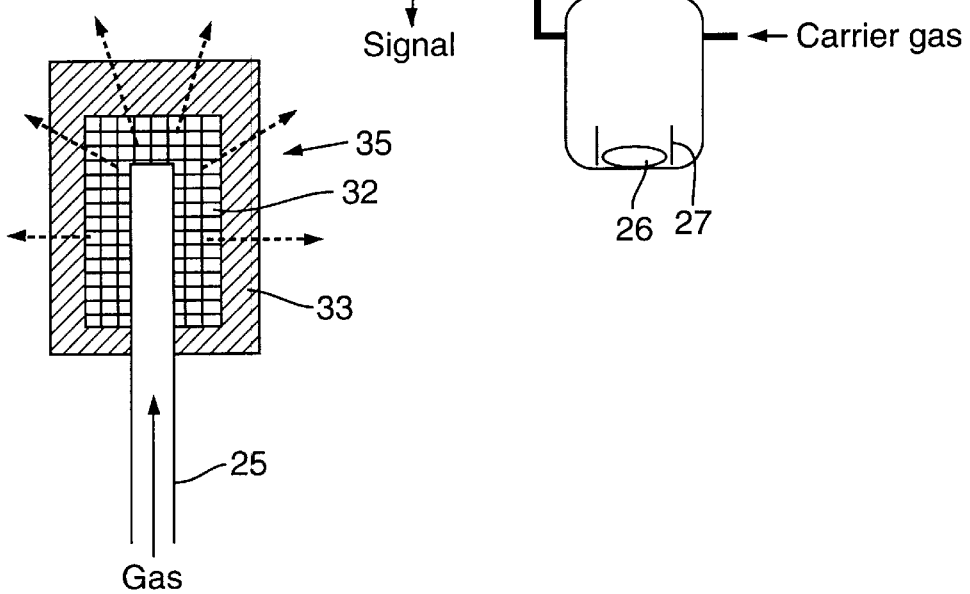
FIG. 4 is a sectional view of a gas-introduction tube, as used with the first embodiment of an apparatus according to the invention, terminating with a muffler.

As shown in FIG. 3, a Teflon conduit 25 is connected to the sample chamber 8. The conduit 25 introduces a gas from a source chamber 24 into the sample chamber 8. As shown in FIG. 4, the conduit 25 terminates in the sample chamber 8 with a muffler 35. The muffler 35 has a double construction of porous ceramic 32 and porous metal 33. The muffler 35 dampens sounds generated as gas is introduced via the conduit 25 into the sample chamber 8. Thus, any effects of such sounds on the target frequency components that will be classified and detected as photoacoustic signals are greatly reduced.

The adhesion gas used in this working example was generated by irradiating a mass of silicone adhesive (as a source material 26) placed in a glass dish 27 in the source chamber 24. The adhesion gas was routed, using a compressor, from the source chamber 24 through the conduit 25 to the sample chamber 8. The carrier gas was air flowing at approximately 5 mL/sec.

The light produced by the light source 1 was adjusted by the light-intensity-adjustment system 2 to an irradiation intensity of approximately 10 $mJ/cm^2$ per pulse. The light (although pulsatile) was continuously irradiated onto the sample 5. Meanwhile, as the sample 5 absorbed each pulse of light, the sample 5 generated a corresponding photoacoustic signal approximately 8 $\mu$sec after each pulse. Each photoacoustic signal was filtered to remove electromagnetic noise and oscillation noise. The main frequency of the acoustic signals in this working example was approximately 150 kHz, and a wavelength close to this frequency was selected and measured by the FFT processor 12.

Figure 5:
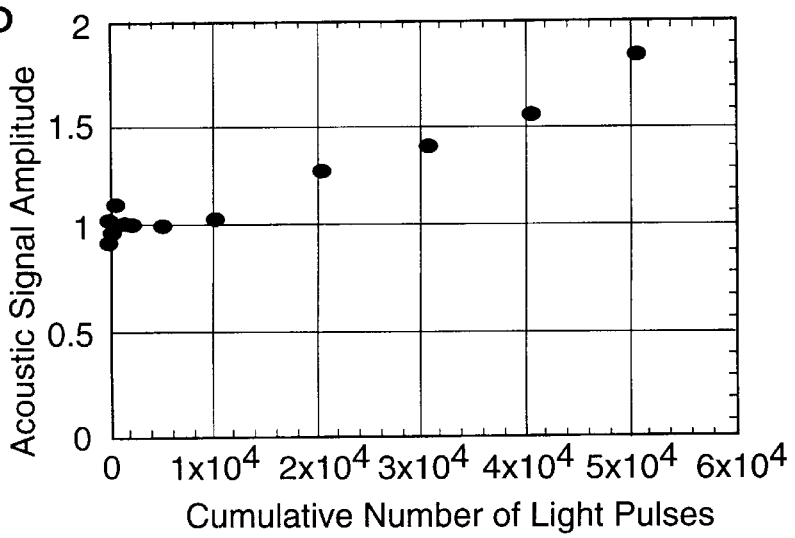
FIG. 5 is a plot of photoacoustic signal amplitude obtained in Working Example 1 when a sample optical component was irradiated by various numbers of pulses of a fixed intensity of light.
Figure 6:
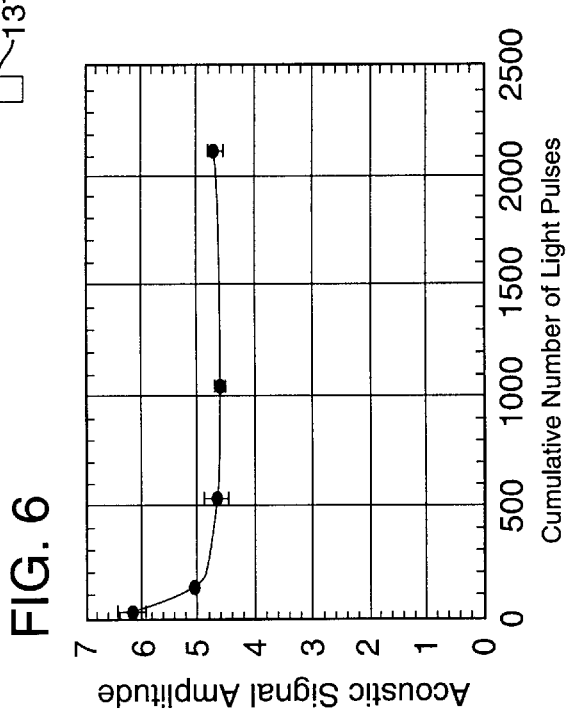
FIG. 6 is a plot of a change in initial photoacoustic signal amplitude obtained in Working Example 1 when a sample optical component was irradiated by various numbers of pulses of a fixed intensity of light.

Representative changes in the amplitude of the photoacoustic signals produced by the sample 5 with continued irradiation by pulses of light of a given intensity are shown in FIG. 5. Representative changes in the initial photoacoustic signal occurring as the sample was irradiated by multiple pulses of fixed-intensity light are shown in FIG. 6. As shown in FIG. 6, the photoacoustic signal amplitude drops during the initial irradiation and thereafter gradually increases as the sample is irradiated with additional pulses of light. This shows that the amount of light absorption drops, upon commencing irradiation of the sample, due to a so-called optical cleaning effect. Thereafter, the amount of light absorption increases as the sample is irradiated further.

The increase in the amplitude of the acoustic signals (corresponding to increases in light absorption by the sample) as the sample is irradiated with additional pulses of light, as shown in FIGS. 5 and 6, is considered to be due to adhesion or absorption of molecules of an adhesion gas to the sample as caused by a photochemical reaction of such molecules.

Comparative Example 1

When photoacoustic signals generated by the sample 5 were measured as described in the first working example but under a condition in which the source chamber 24 was not connected to the sample chamber 8 (i.e., in which the sample chamber 8 contained no gas comprising molecules capable of adhering to or being absorbed by the sample 5), no changes were observed in the photoacoustic signals generated by the sample 5. Also, light absorption by the sample 5 remained constant.

Working Example 2

In this working example, measurements of light absorption by a sample 5 were conducted as described in Working Example 1, except that, in this working example, a gas-collection vessel 23 containing a gas absorbent was connected to the sample chamber 8 (see FIG. 3). The gas inside the sample chamber 8 was collected by the gas-collection vessel 23 during periods in which light absorption measurements were being conducted of the sample 5. After such measurements were complete, the gas collected by the gas-collection vessel 23 was analyzed by GCMS.

The GCMS analysis revealed that the gas comprised several silicone compounds released from the source material 26 in the source chamber 24. These compounds, when adhered to or absorbed by the sample 5, were determined to be responsible for observed changes in light absorption by the sample 5.

The gas-collection vessel 23 proved to be quite effective in collecting gaseous compounds that had an effect on light absorption by the sample 5. These results were further facilitated by an ability, using an apparatus as shown in FIG. 3, to perform quantitative analyses of the gas released from any of various source materials and by an ability, using such apparatus and methods, to standardize conditions (e.g., gas flowrate and collection time) under which gas was introduced into the sample chamber 8.

Working Example 3

In this working example, measurements of changes in light absorption were conducted using an apparatus as used in Working Example 1, except that, in this working example, the sample chamber 8 was provided with gas-introduction ports for introducing nitrogen and water vapor into the sample chamber 8. In addition, the sample chamber 8 included a zirconia-type nitrogen sensor and a polymer thin-film type hygrometer.

The respective rates at which nitrogen and water vapor were added to the sample chamber 8 were controlled while continuously monitoring the concentration of nitrogen and water vapor in the atmosphere inside the sample chamber 8 as measurements were being performed of the photoacoustic signals generated by the sample 5.

The results indicated that addition of nitrogen to the atmosphere inside the sample chamber 8 tended to reduce the amount of gas (generated from the source material) that adhered to or was absorbed by the sample 5. Consequently, it was possible to obtain information on the effects of any of various other gases.

Working Example 4

In this working example, measurements were performed using an apparatus as shown in FIG. 11. The light source 132 was a KrF excimer laser ($\lambda$=248 nm) having a pulse width of approximately 20 ns. The light L1 passed through the light-intensity-adjustment optical system 133a, through the aperture 133b, and through the beamsplitter 134. The resulting light L2 passed through the relay lens 135, the objective lens 136, and the entrance window 124 to irradiate the sample SA. Passage of the light L2 through the relay lens 135 and objective lens 136 caused the light L2 to condense and form an image of the aperture 133a on the surface of the sample SA. The diameter of the irradiation light L2 on the surface of the sample SA was approximately 2 mm. The intensity of the light L2 was regulated by the light-intensity-adjustment optical system 133a (comprising a zoom lens). Light intensity was monitored by the reference-light sensor 137 (bipolar photoelectric tube) located in the light beam L3 reflected by the beamsplitter 134. The beamsplitter 134 was made of quartz glass.

The sample holder 122 was configured to secure a Bakelite® plate (with a V-shaped notch) by clamping from both sides. Acoustic signals generated in the sample SA were detected by the photoacoustic transducer 120 equipped with an aluminum light-receiving plate (not shown) and PZT piezoelectric element. The photoacoustic transducer 120 was secured to the sample SA using conventional vacuum grease. The sample holder 122 was provided with rubber antivibration pads (not shown, but see FIG. 2(b)) arranged as required to provide acoustic isolation of the sample SA.

The sample SA was a quartz glass optical component that was transmissive to the light L2. The sample SA was circular with a diameter of 30 mm and a thickness of 2 mm. The sample SA included a surficial optical thin-film coating 1 $\mu$m thick. The sample SA was mounted in the V-shaped notch of the sample holder 122.

As the light L2 was irradiated onto the sample SA mounted in the sample holder 122, the output of the photoacoustic transducer 120 was measured. Photoacoustic signals were generated (by light absorption) in the sample SA approximately 8 $\mu$sec after each light pulse from the light source 132 impinged on the sample. The acoustic signals were filtered to remove electromagnetic noise and oscillation noise. The main frequency of the acoustic signals in this example was approximately 150 kHz and a wavelength close to this frequency was selected and analyzed using FFT.

During the measurements, the sample SA and the sample holder 122 were situated inside a sealed stainless steel housing 121. The housing 121 included a Teflon gas-inlet port 147 and a Teflon exhaust port 148. The cover 146 was made of glass and was sealed to the housing 121 with a Teflon seal (not shown).

A source material 142 was placed inside the sub-chamber 140 for irradiation by the light beam L4 passing through the window 143 (made of quartz glass). The light beam L4 was produced by diverging a portion of the light L1 using the beamsplitters 134, 144 and passing the light beam L4 through the intensity-adjusting optical system 145 (comprising an array of filters).

The walls 141 of the sub-chamber 140 were configured so as to prevent extraneous light (e.g., scattered from the beam L2 irradiating the sample SA) from irradiating the source material 142. The walls 141 were also configured to allow molecules released from the source material 142 by irradiation to pass into the sample chamber 121 and contact the sample SA.

The source material 142 was a mass of silicone adhesive placed in a glass dish 139 in the sub-chamber 140. As the source material 142 was irradiated with the beam L4, the sample SA was irradiated with the beam L2 at uniform power (approximately 50 mJ/cm² per pulse).

Under such conditions, when changes in the photoacoustic signals generated by the sample SA (indicating the amount of light absorbed by the sample SA) were plotted against the cumulative number of irradiation pulses received by the sample, it was discovered that a reduction in the absorbed light by the sample was initially observed due to the so-called optical cleaning effect. As irradiation of the sample SA proceeded further while allowing molecules of the irradiated source material 142 to enter the sample chamber 121, an increase in light absorption by the sample SA was observed, indicating that such an increase was due to molecules of the source material adhering to or being absorbed by the sample SA.

In a control experiment in which no source material 142 was placed in the sub-chamber 140, signal changes indicating a change in light absorption by the sample SA were not observed.

Figure 12A:
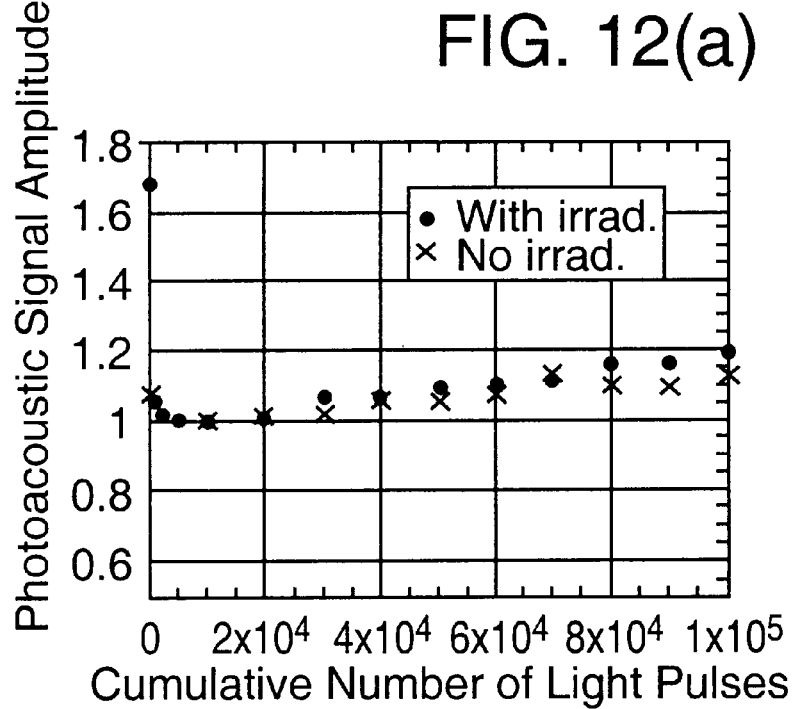
FIGS. 12(a)–12(b) are representative plots of photoacoustic-signal amplitude versus cumulative number of light pulses as obtained in Working Examples 4–6.
Figure 12B:
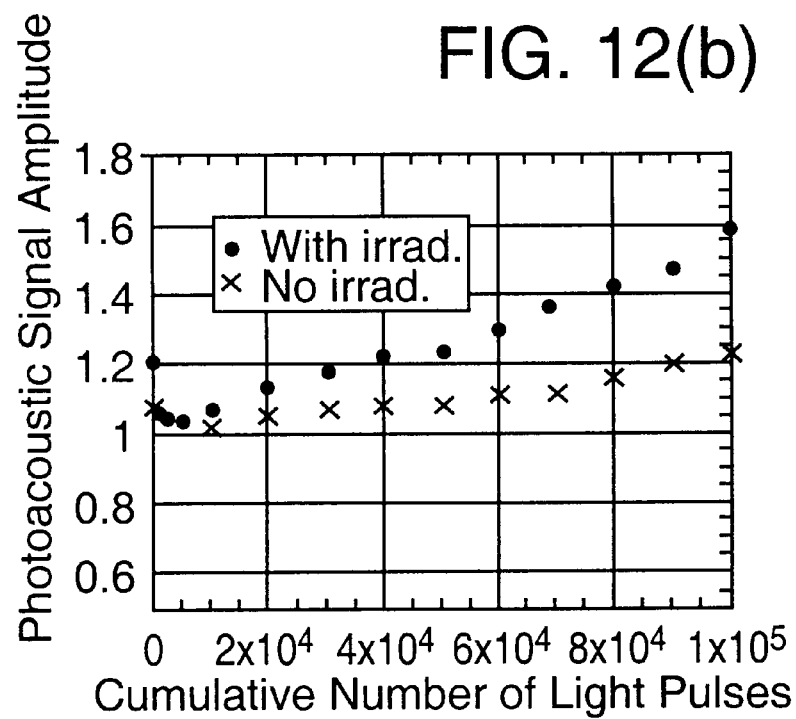

In other control experiments, a comparative measurement was performed in which the intensity of the light L4 irradiating the source material 142 was approximately 0.01% of the intensity of the light L2 irradiating the sample SA, and another comparative measurement was performed in which no light L4 was irradiated onto the source material 142. With a first type of source material, almost no change was observed in the increase of light absorption by the sample due to such reduced irradiation (FIG. 12(a)). With a second type of source material, an increase in absorbed light by the sample was observed (FIG. 12(b)), indicating that adhesion and/or absorption of molecules from the second type of source material still occurred.

Working Example 5

In this working example, photoacoustic measurements were conducted using the apparatus of FIG. 11 and as described above in Working Example 4 except that the light beam L4 used to irradiate the source material 142 was produced by a mercury lamp independently of an excimer laser being used to produce the light beam L2. Such conditions were typical of conditions prevailing during optical cleaning using a mercury lamp.

Under such conditions, the effect of the mercury lamp on generation of gas molecules by a silicone adhesive agent (as a source material 142) were investigated. Whenever the source material 142 was irradiated using the mercury lamp, the light from the KrF excimer laser used to irradiate the sample was effectively blocked from reaching the source material 142.

The results indicated that such irradiation of the source material produced no change in the photoacoustic signals generated during irradiation of the sample compared to when the source material was not irradiated.

Working Example 6

This working example was conducted substantially as described in Working Example 5. Irradiation of the silicone-adhesive source material 142 resulted in the production of volatile low-molecular-weight siloxane. Contact of the sample SA with molecules of the siloxane during irradiation of the sample with KrF laser light caused an increased light absorption by the sample SA. The atmosphere inside the sample chamber 121 was analyzed by collection using the gas-collection vessel 127 followed by GCMS analysis of the collected gas.

Working Example 7

Figure 14:
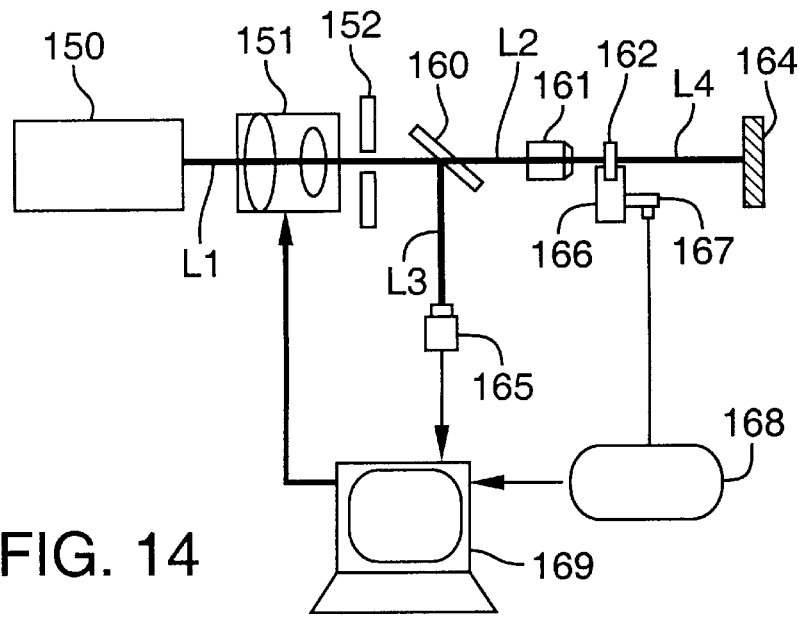
FIG. 14 is a schematic optical diagram of the light-absorption measurement apparatus used in Working Examples 7 and 8.

In this working example, measurements were conducted using the system shown in FIG. 14. The system comprised an ArF excimer laser 150 (λ=193 nm, with a pulse width of approximately 10 ns). The light L1 from the laser 150 passed through a zoom lens 151, through an aperture 152, and through a beamsplitter 160 to become the light beam L2. The light beam L2 passed through an objective lens 161 onto a surface of a sample 162. The objective lens 161 condensed the light L2 and formed an image of the aperture 152 on the surface of the sample 162. The diameter of the light beam as converged on the surface of the sample 162 was approximately 2 mm. The zoom lens 151 controlled the intensity of the light L2. A portion L3 of the light L1 was reflected by the beamsplitter 160 toward the light sensor 165 (bipolar photoelectric tube) that monitored the intensity of the light L3 (and thus of the light L2 irradiating the sample).

Figure 15A:
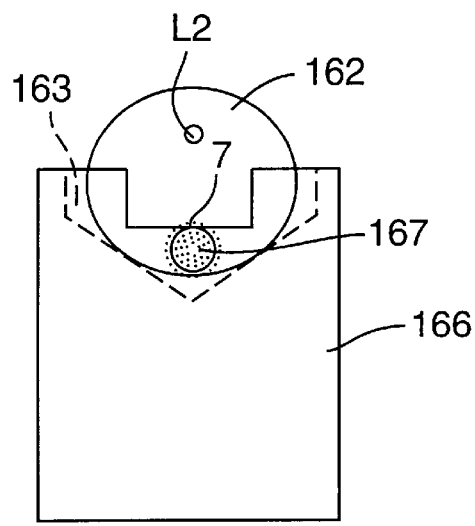
FIGS. 15(a)–15(b) are respective orthogonal elevational views of a sample optical component disposed on a sample holder as used in Working Examples 7 and 8.
Figure 15B:
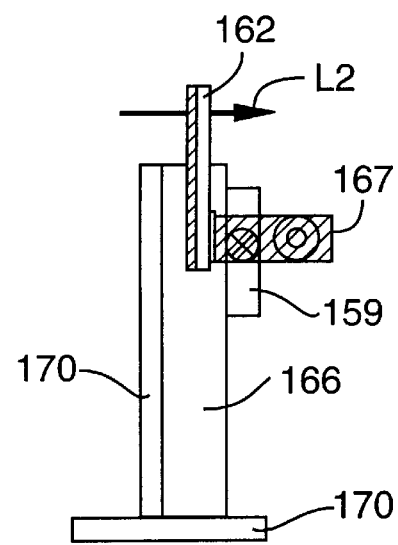

As shown in FIGS. 15(a)–15(b), the sample holder 166 was configured so as to receive the sample 162 in a V-shaped notch 163 formed in the sample holder 166. The sample 162 was effectively secured by clamping on both sides of the sample using a pressure plate 159. Acoustic signals generated in the sample 162 as the sample was irradiated were detected by the photoacoustic transducer 167 (comprising an aluminum receiving plate on PZT). The photoacoustic transducer 167 was secured to the sample 162 using vacuum grease. The sample holder 166 also comprised rubber pads 170 (anti-vibration material) arranged as required to provide acoustic isolation and reduce the generation of sounds outside the sample 162.

The sample 162 was a fluorite glass substrate (transmissive to the wvelength of the light L2) having a thickness of 2 mm and a diameter of 30 mm. The surface of the sample 162 was coated with an optical thin film no greater than 1 μm thick. The sample 162 was mounted in the V-shaped notch 163 of the sample holder 166. As the light L2 from the laser 150 irradiated the sample 162, photoacoustic signals generated in the sample 162 after each pulse of light were received by the photoacoustic transducer 167.

Photoacoustic signals generated by the sample 162, upon absorbing light pulses, occurred approximately 8 μsec after each light pulse. The photoacoustic signals were filtered to remove electromagnetic noise and oscillation noise. The main frequency of the photoacoustic signals in this example was approximately 150 kHz. Frequency analysis of the photoacoustic signals was conducted using an FFT processor 168 and computer 169.

Photoacoustic signals were initially detected at a light-irradiation power at which both the thin film and the optical sample 162 itself did not undergo any change in light absorption. Then, the light-irradiation power was slightly increased such that the sample 162 was irradiated with a uniform power of at least 200 mJ/cm² per pulse. Changes in the photoacoustic signals (representing the amount of light absorbed) generated by the sample 162 as a function of the number of the cumulative number of irradiation "shots" (pulses) were observed.

Figure 16:
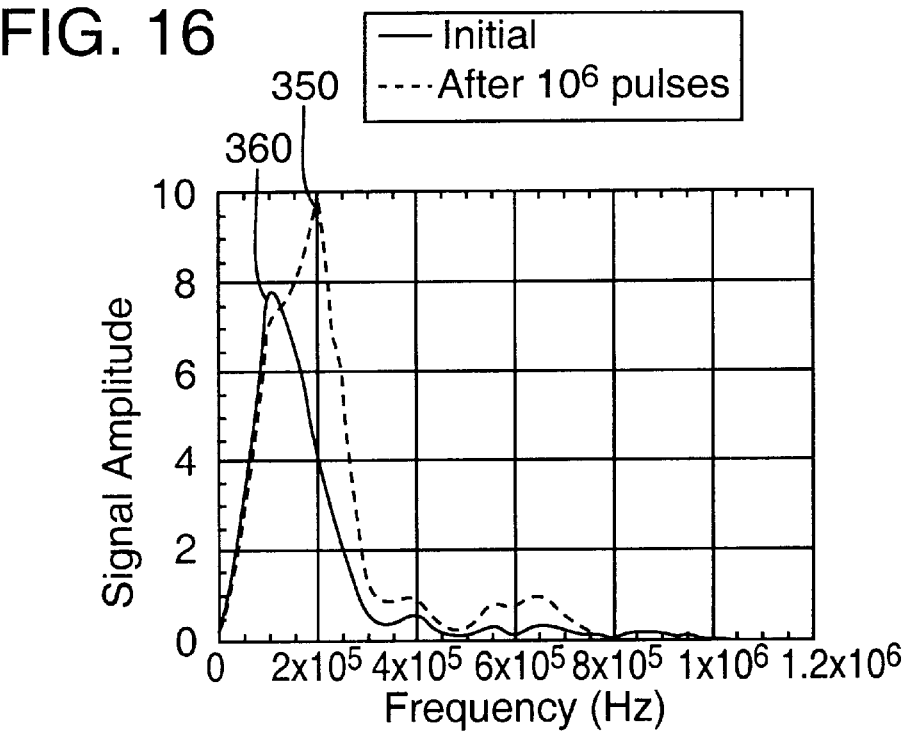
FIG. 16 is a representative plot of signal amplitude versus frequency of an acoustic signal produced whenever a thin-film and underlying optical component degrade simultaneously upon exposure to light.

As shown in FIG. 16, when a light-absorption change occurred only in the optical thin film and not in the fluorite sample itself, only the amplitude of the frequency curve produced by the FFT processor 168 changed without significant change to the waveform. Thus, a change in light absorption by the thin film can be monitored by plotting changes in the amplitude of the main frequency component (curve 360). In contrast, when a change in light absorption occurred in the fluorite sample itself, the appearance of a satellite peak (curve 350) was observed which made it possible to sufficiently detect increases in light absorption of the sample itself by monitoring changes in light absorption.

Working Example 8

This working example is directed to detecting light absorption by, and adhesion of extraneous molecules to, a sample. To such end, acoustic signals generated by the sample are measured while the sample is in a controlled atmosphere.

Figure 17:
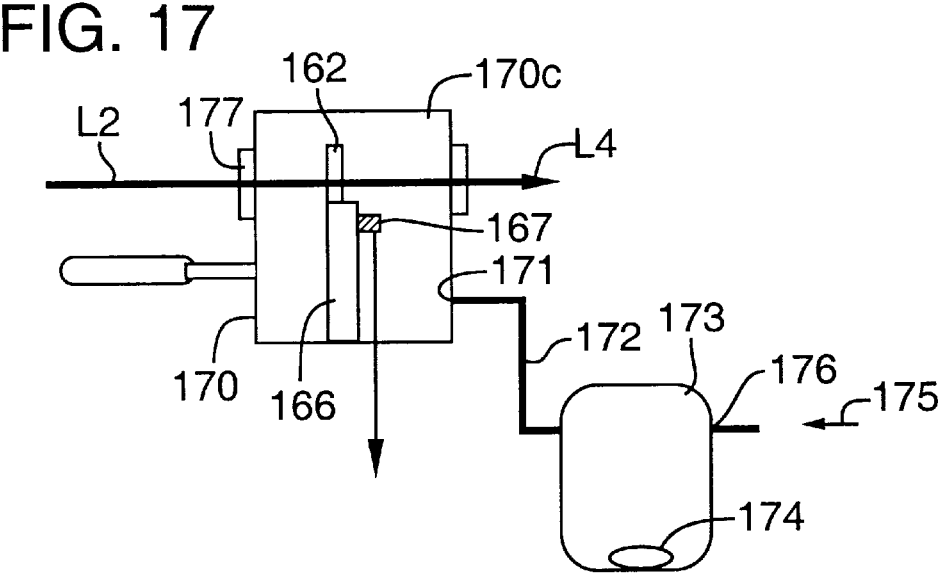
FIG. 17 is a schematic elevational view of a sample chamber connected to a source chamber as used in Working Example 8.

The apparatus used was generally as used in Working Example 7 (FIGS. 14 and 15(a)–15(b)), except that a stainless steel sample chamber 170 was used as shown in FIG. 17. The sample 162 and sample holder 167 were placed inside the sample chamber 170. The sample chamber 170 also comprised an inlet 171 connected to a conduit 172 (made of Teflon) that connected the sample chamber 170 to a source chamber 173. The sample chamber 170 included a glass cover 170c sealable to the sample chamber 170 with a Teflon seal. The source chamber 173, made of glass, contained a mass 174 of a silicone adhesive that served as a source of gaseous molecules that adhered to or were absorbed by the sample 162. Gas released from the adhesive 174 filled the source chamber 173. A carrier gas (arrow 175) entered the source chamber 173 through a carrier-gas inlet 176. The resulting mixture of carrier gas and gas released from the adhesive 174 flowed through the conduit 172 and entered the sample chamber 170. In this working example, the carrier gas was pure air delivered from a compressor (not shown) at approximately 5 mL/sec.

The sample 162 was irradiated by a light beam L2 from the laser 150. The light beam L2 entered the sample chamber 170 through a window (quartz) 177. As the sample 162 was irradiated in such a manner with the light beam L2, any changes in the frequency components of the photoacoustic signals generated by the sample were detected as described above in Working Example 7. Changes in the amplitude of the main frequency components (e.g., curve 360 in FIG. 16) were detected following adhesion and/or absorption on the sample 162 of molecules of the gas released from the source material 174. Light-induced changes to the sample 162 itself yielded a change in other frequency components (e.g., appearance of satellite peaks).

By plotting the respective amplitudes of the main frequency components, the degree of adhesion and absorption of gas molecules on the surface of the sample 162 could be found. It was concluded that degradation of the sample itself was manifest by the changes in the satellite peaks.

Whereas the invention has been described in connection with multiple embodiments and examples, it will be apparent that the invention is not limited to those embodiments and examples. On the contrary, the invention is intended to encompass all modifications, alternatives, and equivalents as may be included within the spirit and scope of the invention as defined by the appended claims.

What is claimed is:

1. An apparatus for measuring changes in light absorption exhibited by an optical component upon exposure of the optical component to light, the apparatus comprising:
   (a) a sample holder configured to hold a sample optical component as the sample is exposed to light;
   (b) a sensor configured and situated to detect absorbance of light by the sample as the sample is exposed to the light;
   (c) a sample-chamber housing configured to contain the sample holder holding the sample as the sample is exposed to the light, the sample-chamber housing defining a sample chamber; and
   (d) a gas-introduction port for conducting a specified gas from a source into the sample chamber.

2. The apparatus of claim 1, further comprising a gas-inlet-control unit situated and configured so as to control an amount of the gas introduced into the sample chamber through the gas-introduction port.

3. The apparatus of claim 1, wherein the specified gas comprises molecules that can attach to the sample in a way that can result in a change in light absorbance by the sample.

4. The apparatus of claim 1, wherein the housing is further configured to contain a source material of molecules that can attach to the sample in a way that can result in a change in light absorbance by the sample.

5. The apparatus of claim 4, wherein the gas is a carrier gas.

6. The apparatus of claim 4, wherein the housing defines a sub-chamber for containing the source material.

7. The apparatus of claim 6, wherein the sub-chamber is separated from the sample chamber by a partition that blocks scattered light from passing from the sample chamber to the sub-chamber and from the sub-chamber to the sample chamber while allowing the molecules of the source material to pass from the sub-chamber to the sample chamber.

8. The apparatus of claim 7, wherein the housing defines a first window transmissive to a first light and a second window transmissive to a second light, the first window being situated so as to allow the first light to pass through the first window to the sample in the sample chamber, and the second window being situated so as to allow the second light to pass through the second window to the source material in the sub-chamber.

9. The apparatus of claim 1, wherein the housing comprises a window transmissive to the light, the window being situated so as to allow the light to pass from a light source external to the housing to the sample in the sample chamber.

10. The apparatus of claim 1, wherein the sensor comprises a photoacoustic transducer and a fast-fourier-transform processor connected to the photoacoustic transducer.

11. An apparatus for measuring changes in light absorption exhibited by an optical component upon exposure of the optical component to light, the apparatus comprising:
   (a) a sample holder configured to hold a sample optical component as the sample is exposed to pulses of light;
   (b) a photoacoustic transducer configured and arranged to detect photoacoustic signals generated by the sample as the sample is exposed to pulses of the light;
   (c) a sample chamber configured to contain the photoacoustic transducer and the sample holder holding the sample as the sample is exposed to the pulses of light, the sample chamber defining a space; and
   (d) a gas-introduction port for conducting a specified gas from a source into the space defined by the sample chamber.

12. The apparatus of claim 11, wherein the gas comprises molecules that can adhere to or be absorbed by the sample.

13. The apparatus of claim 11, further comprising a source of the gas connected to the gas-introduction port.

14. The apparatus of claim 13, wherein the source of the gas is a source chamber connected via a conduit to the gas-introduction port, the source chamber being configured to contain a source material that, when irradiated by light, releases molecules of a compound that can adhere to or be absorbed by the sample in a way that can cause a change in light absorption by the sample.

15. The apparatus of claim 13, wherein the gas-introduction port comprises a gas-inlet-control unit situated and configured so as to control an amount of the gas introduced into the sample chamber through the gas-introduction port from the source.

16. The apparatus of claim 11, further comprising a gas sensor situated and configured to quantitatively determine a concentration of the specified gas in the space defined by the sample chamber.

17. The apparatus of claim 11, wherein the sample chamber comprises a material exhibiting a predetermined degassing of molecules into the space.

18. The apparatus of claim 17, wherein:
the sample chamber comprises walls each having an interior-facing surface; and
the material is configured into a liner for the interior-facing surfaces.

19. The apparatus of claim 18, wherein the material is aluminum.

20. The apparatus of claim 18, wherein the liner is replaceable after each one or more uses.

21. The apparatus of claim 11, wherein the sample container is replaceable after each one or more uses.

22. An apparatus for measuring a change in light absorption exhibited by an optical component upon exposure of the optical component to light, the apparatus comprising:
(a) a first light source operable to produce a first light;
(b) a source chamber configured to contain a source material as the source material is irradiated by the first light, the first light having a wavelength sufficient to cause the source material to produce, during such irradiation by the first light, molecules of an adhesion gas;
(c) a second light source operable to produce pulses of a second light;
(d) a sample holder configured to hold a sample optical component as the sample is exposed to pulses of the second light;
(e) a sensor configured and arranged to detect absorbance of the second light by the sample;
(f) a sample chamber defining a space, the sample chamber configured to contain within the space the sensor and the sample holder holding the sample as the sample is exposed to the pulses of the second light; and
(g) a conduit for routing molecules of the adhesion gas from the source chamber to the sample chamber so as to expose the sample to the molecules of the adhesion gas as the sample is being exposed to the second light.

23. The apparatus of claim 22, further comprising a light-intensity-adjustment optical system situated and configured to receive the second light and to adjust an intensity of the second light reaching the sample.

24. The apparatus of claim 23, further comprising a beamsplitter, wherein the source of the first light and the source of the second light are a pulsatile laser, the laser producing a light beam of which a first portion is reflected by the beamsplitter to become the first light and a second portion is transmitted by the beamsplitter to become the second light.

25. The apparatus of claim 22, further comprising a light blocker situated and configured to prevent stray light, including scattered light generated when the sample is irradiated by the second light, from irradiating the source material.

26. The apparatus of claim 22, wherein the sensor comprises a photoacoustic sensor in acoustic contact with the sample, the photoacoustic sensor being operable to measure an acoustic signal generated by expansion and contraction of the sample resulting from impingement on the sample of a pulse of the second light that causes an instantaneous heating a cooling of the sample.

27. The apparatus of claim 22, further comprising a gas analyzer configured and situated to obtain data regarding identity and concentration of the adhesion gas.

28. A method for measuring light absorption exhibited by an optical component sample as the optical component sample is irradiated with a light, the method comprising the steps:
(a) mounting the sample in a sample holder;
(b) placing the sample and sample holder in a sealed environment that can contain molecules of a gas that can adhere to or be absorbed by a surface of the sample;
(c) irradiating the sample with pulses of a first light while exposing the sample to the molecules of the gas in the sealed environment containing molecules of the gas; and
(d) as each pulse of the first light impinges on the sample, measuring an acoustic signal generated in the sample due to exposure to the pulse, the acoustic signal being a function of an amount of light energy absorbed by the sample from the light pulse.

29. The method of claim 28, further comprising the step of generating an electrical signal corresponding to the acoustic signal.

30. The method of claim 29, further comprising the step of performing a fast fourier transform of the electrical signal.

31. The method of claim 28, further comprising the steps of:
irradiating a source material with a second light to cause the source material to produce molecules of the gas; and
conducting the molecules of the gas to the sealed environment so as to contact the sample as the sample is being exposed to the first light in the sealed environment.

32. A method for measuring light absorption exhibited by an optical component sample as the sample is irradiated with a light, the method comprising the steps of:
(a) providing a sealable sample chamber;
(b) placing the sample in the sample chamber and sealing the sample chamber;
(c) providing molecules of an adhesion gas;
(d) while introducing the molecules of the adhesion gas into the sample chamber, irradiating the sample in the sample chamber with pulses of a light suspected of causing the sample to exhibit a change in absorption of the first light with cumulative exposure of the sample to pulses of the light; and
(e) measuring the absorption by the sample of the pulses of the light.

33. The method of claim 32, wherein step (a) comprises providing a sample chamber defined by walls exhibiting low degassing.

34. The method of claim 32, wherein step (a) comprises providing a sample chamber defined by walls lined with a material exhibiting low degassing.

35. A method for measuring light absorption exhibited by an optical component sample as the sample is irradiated with a light, the method comprising the steps of:
(a) irradiating the sample with a pulse of a light suspected of causing the sample to exhibit a change in absorption of the light with cumulative exposure of the sample to pulses of the light;

(b) as the pulse of the light impinges on the sample, measuring an acoustic signal generated in the sample due to exposure to the pulse, the acoustic signal having a waveform that is a function of an amount of light energy absorbed by the sample from the light pulse and being generated by an expansion and contraction of the sample due to an instantaneous heating of the sample as the sample receives and absorbs at least a portion of the light pulse and a subsequent cooling of the sample after the light pulse; and (c) determining from the waveform, generated as the sample received the pulse of the light, a first waveform component arising from absorption of light from the pulse on a surface of the sample and a second waveform component arising from absorption of light from the pulse within a depth dimension of the sample.

36. The method of claim 35, wherein step (c) further comprises:

separating the first waveform component from the second waveform component;

breaking down the first and second waveform components into respective constituent frequency components; and comparing the amplitude of the frequency components of the first waveform with the amplitude of the frequency components of the second waveform.

37. The method of claim 35, further comprising the step of comparing information obtained in step (c) with corresponding information obtained in step (c) from an earlier pulse irradiated on the sample.

38. The method of claim 35, further comprising the step of comparing information obtained in step (c) with corresponding information previously obtained in step (c) from irradiating a different sample with a pulse of the light.

* * * * *

UNITED STATES PATENT AND TRADEMARK OFFICE
CERTIFICATE OF CORRECTION

PATENT NO. : 6,108,096
DATED : August 22, 2000
INVENTOR(S) : Yoshijiro Ushio, Toru Nakamura, Sumito Shimizu and Tetsuya Oshino It is certified that error appears in the above-identified patent and that said Letters Patent is hereby corrected as shown below:

Title page,
Add the following:
--[30]  Foreign Application Priority Data

December 22, 1997 [JP] Japan ................................9-353417
March 6, 1998 [JP] Japan .......................................10-071230
September 3, 1998 [JP] Japan .................................10-250070
October 12, 1998 [JP] Japan ...................................10-289176

Column 5,
Line 43, change "heating a cooling" to -- heating or cooling --

Column 11,
Line 27, change "it preferable" to -- it is preferable --

Column 14,
Line 9, change "to made of" to -- to be made of --
Line 49, change "signals is" to -- signal is --

Column 15,
Line 53, change "128a, 128." to -- 128a, 128b. --
Line 61, change "121 Hence," to -- 121. Hence, --

Column 16,
Line 62, change "SA Photoacoustic" to -- SA. Photoacoustic --

Column 18,
Line 1, change "if an a source" to -- if a source --

UNITED STATES PATENT AND TRADEMARK OFFICE
CERTIFICATE OF CORRECTION

PATENT NO.  : 6,108,096
DATED       : August 22, 2000
INVENTOR(S) : Yoshijiro Ushio, Toru Nakamura, Sumito Shimizu and Tetsuya Oshino It is certified that error appears in the above-identified patent and that said Letters Patent is hereby corrected as shown below:

Column 21,
Lines 14-15, change "L2." to -- L2). --

Column 28,
Line 32, change "wvelenght" to -- wavelength --

Column 32,
Line 5, change "heating a cooling" to -- heating or cooling --

Signed and Sealed this

Twenty-first Day of August, 2001

*Attest:*

NICHOLAS P. GODICI
*Attesting Officer*     *Acting Director of the United States Patent and Trademark Office*